(12) United States Patent
Sen et al.

(10) Patent No.: US 12,144,997 B2
(45) Date of Patent: Nov. 19, 2024

(54) BI-PHASIC QUASI-STATIC BRAIN COMMUNICATION DEVICE AND METHOD

(71) Applicant: Purdue Research Foundation, West Lafayette, IN (US)

(72) Inventors: Shreyas Sen, West Lafayette, IN (US); Baibhab Chatterjee, West Lafayette, IN (US); Mayukh Nath, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 412 days.

(21) Appl. No.: 17/560,525

(22) Filed: Dec. 23, 2021

(65) Prior Publication Data
US 2022/0193427 A1 Jun. 23, 2022

Related U.S. Application Data

(60) Provisional application No. 63/129,591, filed on Dec. 23, 2020.

(51) Int. Cl.
*A61N 1/378* (2006.01)
*A61N 1/372* (2006.01)
(Continued)

(52) U.S. Cl.
CPC ....... *A61N 1/3787* (2013.01); *A61N 1/37223* (2013.01); *A61N 1/3727* (2013.01); *H04B 13/005* (2013.01); *H02J 50/001* (2020.01)

(58) Field of Classification Search
CPC ........ H04B 13/00; H04B 13/005; A61N 1/10; A61N 1/18; A61N 1/20; A61N 1/32;
(Continued)

(56) References Cited

U.S. PATENT DOCUMENTS

| | | | |
|---|---|---|---|
| 8,547,248 B2 * | 10/2013 | Zdeblick | A61M 5/172 600/549 |
| 8,577,327 B2 * | 11/2013 | Makdissi | A61N 1/37288 455/343.1 |

(Continued)

FOREIGN PATENT DOCUMENTS

| | | | | |
|---|---|---|---|---|
| WO | WO-2006040095 A2 * | 4/2006 | | H04B 13/005 |
| WO | WO-2014096971 A2 * | 6/2014 | | A61N 1/0534 |
| WO | WO-2018208990 A1 * | 11/2018 | | A61B 5/0031 |

OTHER PUBLICATIONS

Method, Circuit and System for Transferring Signals via the Human Body, WO 2006040095 A2 (English Text), Fasshauer Peter, Apr. 20, 2006. (Year: 2006).*

(Continued)

*Primary Examiner* — Quochien B Vuong
(74) *Attorney, Agent, or Firm* — Purdue Research Foundation

(57) ABSTRACT

A system and method for brain-machine interface communication utilizing Bi-Phasic Quasi-Static Brain Communication (BP-QBC). The system includes a first device and a second device that are in wireless communication together. The system and method include signal transmission between the first device and the second device through dipole coupling. The system is configured to utilize compressive sensing and collision avoidance for enhanced net energy efficiency. The system and method utilize fully electrical quasi-static signaling to militate against energy transduction losses.

12 Claims, 28 Drawing Sheets

(51) Int. Cl.
*H04B 13/00* (2006.01)
*H02J 50/00* (2016.01)

(58) Field of Classification Search
CPC ...... A61N 1/37; A61N 1/372; A61N 1/37211;
A61N 1/37217; A61N 1/37223; A61N
1/3727; A61N 1/378; A61N 1/3787; H02J
50/001; H02J 2310/23
See application file for complete search history.

(56) References Cited

U.S. PATENT DOCUMENTS

| | | | |
|---|---|---|---|
| 10,307,594 B2* | 6/2019 | Pepin | A61N 1/36125 |
| 10,335,596 B2* | 7/2019 | Yakovlev | A61N 1/0553 |
| 11,097,096 B2* | 8/2021 | Linden | A61N 1/36117 |
| 2006/0161216 A1* | 7/2006 | John | A61N 1/3605 607/40 |
| 2016/0303301 A1* | 10/2016 | Bluvshtein | A61M 60/876 |
| 2019/0143126 A1* | 5/2019 | Wheeler | A61N 1/37288 607/60 |

OTHER PUBLICATIONS

Borton, D. et al., "An implantable wireless neural interface for recording cortical circuit dynamics in moving primates," J. Neural Eng. 2013.
Lim, J. et al., A 0.19x0.17mm2 Wireless Neural Recording IC for Motor Prediction with Near-Infrared-Based Power and Data Telemetry, ISSCC 2020.
Ghanbari, M. et al., A 0.8mm3 Ultrasonic Implantable Wireless Neural Recording System with Linear AM Backscattering, ISSCC 2019, Session 17, Technologies for Human Interaction & Health, 17.5.
Yu, Z. et al., An 8.2 mm3 Implantable Neurostimulator with Magnetoelectric Power and Data Transfer, ISSCC 2020.
Jia, Y. et al., A mm-Sized Free-Floating Wirelessly Powered Implantable Optical Stimulating System-on-a-Chip, ISSCC 2018.
Lo, Y. et al., A 176-Channel 0.5cm3 0.7g Wireless Implant for Motor Function Recovery After Spinal Cord Injury, ISSCC 2016.
Lee, J et al., An Implantable Wireless Network of Distributed Microscale Sensors for Neural Applications, Int. IEEE/EMBS Conference on Neural Engineering (NER), 2019.
ICNIRP Guidelines for Limiting Exposure to Time-Varying Electric, Magnetic and Electromagnetic Fields, Available: https://www.icnirp.org/cms/upload/publications/ICNIRPemfgdl.pdf., 1998.
Yuk, B. et al., An Implantable Body Channel Communication System With 3.7-pJ/b Reception and 34-pJ/b Transmission Efficiencies, IEEE Solid-State Circuits Letters, 2020.
"NEVA (Bio)Electromagnetics," Web page < https://www.nevaelectromagnetics.com/>, Accessed: Jan. 5, 2020, retrieved from Internet Archive Wayback Machine < https://web.archive.org/web/20200803095141/https://www.nevaelectromagnetics.com/> on Aug. 23, 2020.
"Tissue Properties from Gabriel-Gabriel Model.," Web page <https://itis.swiss/virtual-population/tissue-properties/database/dielectric-properties/>, Accessed: Jan. 5, 2020, retrieved from Internet Archive Wayback Machine <https://web.archive.org/web/20190503184222/https://itis.swiss/virtual-population/tissue-properties/database/dielectric-properties/> on May 3, 2019.
Chatterjee, B. et al., A 1.15µW 5.54mm3 Implant with a Birdirectional Neural Sensor and Stimulator SoC Utilitizing Bi-Phasic Quasi-static Brain Communication Achieveing 6kbps-10Mbps Uplink with Compressive Sensing and RO-PUF Based Collision Avoidance, 2021 Symposium on VLSI Circuits Digest of Technical Papers, 978-4-86348-780-2 ©2021 JSAP.
Roberts, N. et al., A 236nW -56.5dBm-Sensitivity Bluetooth Low-Energy Wakeup Receiver with Energy Harvesting in 65nm CMOS, ISSCC 2016, Session 26, Wireless for IoE, 26.8.
Musk, E. and Neuralink, An Integrated Brain-Machine Interface Platform with Thousands of Channels, bioRxiv, posted online Jul. 17, 2019, doi: http://dx.doi.org/10.1101/703801.
Singer, A. et al., Magnetoelectric Materials for Miniature, Wireless Neural Stimulation at Therapeutic Frequencies, Neuron 107, 1-13, Aug. 19, 2020 @2020 Elsevier Inc.

\* cited by examiner

"PRIOR ART"

"PRIOR ART"

BI-PHASIC QUASI-STATIC BRAIN COMMUNICATION DEVICE AND METHOD

CROSS REFERENCE TO RELATED APPLICATIONS

This application claims the benefit of U.S. Provisional Application Ser. No. 63/129,591, filed on Dec. 23, 2020. The entire disclosure of the above application is hereby incorporated herein by reference.

FIELD

The present disclosure relates to communication systems and, more particularly, to surgically implantable, wireless communication systems.

INTRODUCTION

This section provides background information related to the present disclosure which is not necessarily prior art.

Brain-machine interfaces (BMIc) or neural interfaces hold promise for the restoration of sensory and motor function and the treatment of neurological disorders. This technology may be applicable in a variety of industries that address certain needs such as psychological disorders, Parkinson's disease, Alzheimer's disease, and prosthetics. One specific example of this technology may include the NEURALINK® implant. However, known BMIc require tethered data transmission and wired power delivery which may increase the likelihood of patient cortical scarring, gliosis, infection, and cerebrospinal fluid (CSF) leakage. Known tethered BMIc systems may be uncomfortable for the patient and may require surgery to remove and/or provide maintenance to.

There is a need to develop a low power wireless communication system that is capable of harvesting power/energy in the implantable device. Attempts of untethered miniaturized wireless neural sensors and stimulators have been demonstrated with various data/power transmission modalities, but each attempt has included their own shortfalls including tissue absorption/scatter, skull absorption, device form-factor, transduction efficiency, and robustness. For instance, the use of Radio Frequency (RF) transmission suffers from increased tissue absorption, requiring increased transmitter power Tx (for instance, 0.5 W, which exceeds ICNIRP safety guidelines by around ten-fold). Optical (OP) and Ultrasonic (US) telemetry are indicated to be safer than RF transmission, but they come at the cost of significant transmission loss due to scattering and skull absorption (for instance, 110 dB loss), requiring a sub-cranial interrogator which needs to be surgically placed, and reduces end-to-end efficiency. Magneto-Electric (ME) methods exhibit low tissue-absorption but have large transduction loss (for instance, 0.1 mT magnetic field, equivalent to ~300 kV/m electric field requirement for isoenergy-density). Such inefficiencies necessitate higher transfer powers to be transmitted through the brain tissue of the patient. These higher transfer powers may lead to interfering with physiological signals and may unintentionally stimulate the brain tissue.

There is a continuing need for a wireless communication system that is capable of harvesting power/energy in an implantable device, reduces the necessary power to operate, and efficiently transfers data.

SUMMARY

In concordance with the instant disclosure, a wireless communication system that is capable of harvesting power/energy in an implantable device, reduces the necessary power to operate, and efficiently transfers data, has been surprisingly discovered.

In one embodiment, a wireless communication system includes a first device and a second device. The first device may include a data transmitter, a data receiver, and an energy harvester. The first device may be configured to be substantially implanted within the patient. In a specific example, the first device may be completely implanted into the brain of the patient. The second device may include a data receiver, a data transmitter, and a power transmitter. The second device may be in wireless Bi-Phasic Quasi-Static Brain Communication (BP-QBC) with the first device. The BP-QBC may be enabled by the wireless communication system where a modulated electro-quasistatic signal is coupled to the internal tissue of the patient through a plurality of electrodes. In a specific example, the first device may include a first electrode and a second electrode. With continued reference to the specific example, the first device may utilize dipole coupling to create an electric field between the first electrode and the second electrode. The second device may be configured to be disposed substantially epicutaneously on the patient. The wireless BP-QBC from the first device to the second device may include an electrical uplink channel and the wireless BP-QBC from the second device to the first device includes an electrical downlink channel.

In another embodiment, the present technology includes methods of using the wireless communication system for a patient. For instance, a first method of using the wireless communication system may include providing a first device including a data transmitter, a data receiver, an energy harvester, a first device electrode, and a capacitor electrically coupled to the first device electrode. In a specific example, the first device electrode may include a plurality of electrodes. The method may also include providing a second device including a data receiver, a data transmitter, and a power transmitter. An input signal may be received at the data receiver of the first device. In a specific example, the input signal may include an input configuration signal received at the first device data receiver. In another specific example, the input signal may be a biological signal received at the first device electrode(s). The input signal may be processed into a bi-phasic signal. The bi-phasic signal may then be transmitted through the tissue of the patient. Afterwards, the bi-phasic signal may be received at the data receiver of the second device.

In certain circumstances, the wireless communication system may be used according to a second method. The second method may include providing a first device including a data transmitter, a data receiver, an energy harvester, a first device electrode, and a capacitor electrically coupled to the first device electrode. The method may also include providing a second device including a data receiver, a data transmitter, and a power transmitter. An alternating electrical signal may be generated in the power transmitter of the second device. An electrical configuration signal may also be generated in the power transmitter of the second device. The alternating electrical signal and the electrical configuration signal may be modulated in the power transmitter of the second device, thereby creating a modulated alternating electrical signal. The modulated alternating electrical signal may be transmitted from an electrode of the second device to the first device. Afterwards, the electrical configuration signal from the modulated alternating electrical signal may be decoded in the first device. Then, the first device may generate DC power from the modulated alternating electrical signal.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

DETAILED DESCRIPTION

Figure 1:
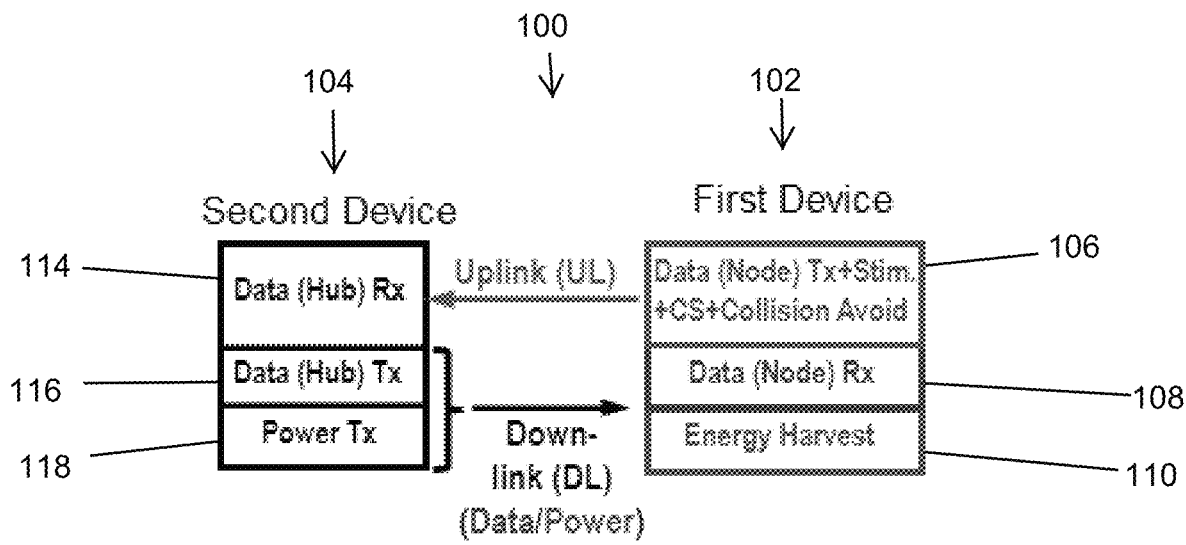
FIG. 1 is a schematic diagram of a wireless communication system, according to one embodiment of the present disclosure.
Figure 2:
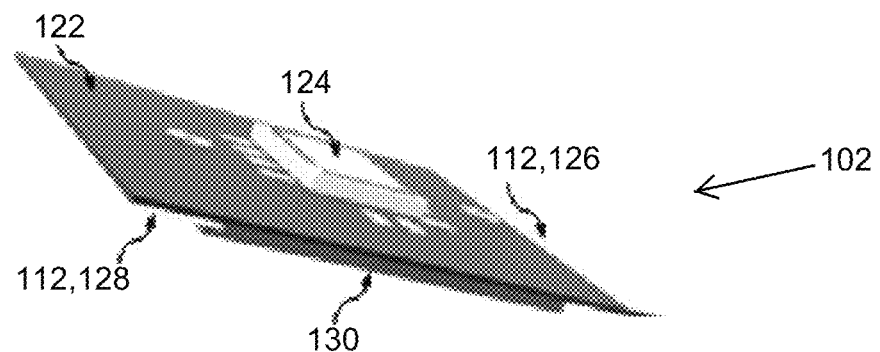
FIG. 2 is a top perspective view of a first device of the wireless communication system, according to one embodiment of the present disclosure.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature unless otherwise disclosed, and thus, the order of the steps can be different in various embodiments, including where certain steps can be simultaneously performed.

I. Definitions

Unless otherwise defined, all technical terms used herein have the same meaning as commonly understood by one of ordinary skill in the art to which the present disclosure pertains.

As used herein, the terms "a" and "an" indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As used herein, the term "bi-phasic quasi-static brain communication" may refer to a fully electric and quasistatic mode of data signal transference between two or more devices. The "bi-phasic quasi-static brain communication" may also include that the data signal switches on more than one side and/or direction from a reference potential.

As used herein, the term "epicutaneously" refers to something that is made, done, or effected directly upon the skin.

As used herein, the term "DC power" refers to a one-directional flow of electric charge, or otherwise known as "direct current."

As used herein, the term "sparsifying" refers to dispersing or separating.

As used herein, the terms "subject" and "patient" may be used interchangeably and refer to any vertebrate organism.

As used herein, the term "discrete wavelet transform" may be understood as a mathematical tool that provides a frequency information as well as a location-in-time information, when applied to a signal. In signal processing, this is useful in separating out (or sparsifying) important information present in the signal which helps in data compression.

In the present disclosure the terms "about" and "around" may allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

II. Description

Figure 7:
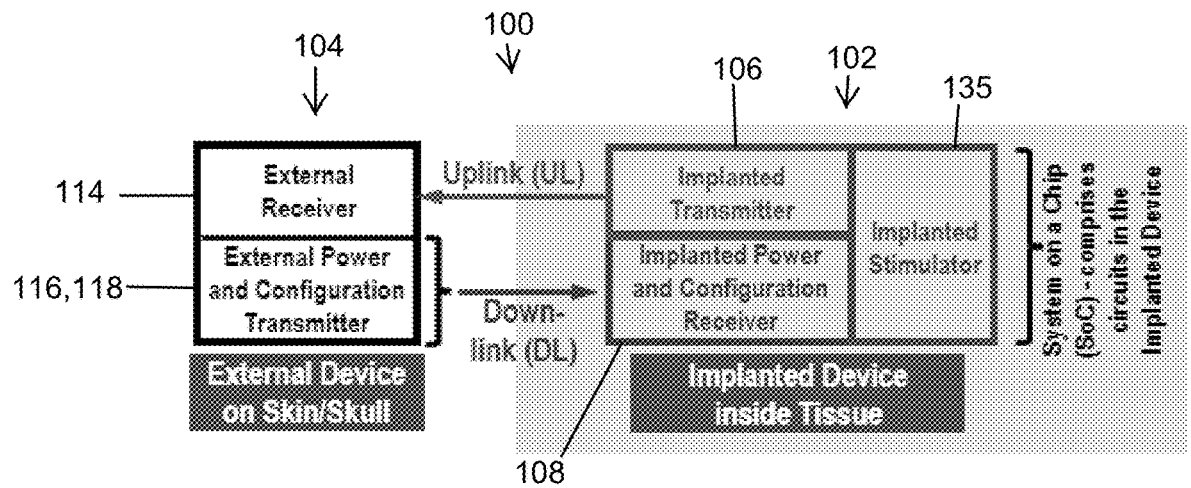
FIG. 7 is a schematic diagram of the wireless communication system, according to one embodiment of the present disclosure.

As shown in FIGS. 1 and 7, a wireless communication system 100 includes a first device 102 and a second device 104. With reference to FIGS. 1, 7, 13 and 42, the first device 102 may include a first device data transmitter 106, a first device data receiver 108, and an energy harvester 110. The first device data transmitter 106 may include a first device electrode 112. The first device 102 may be configured to be substantially implanted within the patient. In a specific example, the first device 102 may be completely implanted into the brain of the patient. In certain circumstances, the first device 102 may be utilized as a reference potential. The first device data receiver 108 may also be known as the implanted power and configuration receiver or as the first device power and configuration receiver. As shown in FIGS. 1 and 7, the second device 104 may include a second device data receiver 114, a second device data transmitter 116, and a power transmitter 118. The second device data transmitter 116 and the second device power transmitter 118 may also collectively be known as the external power and configuration transmitter or the second device power and configuration transmitter. The second device 104 may include a second device electrode 120. The second device 104 may be in wireless Bi-Phasic Quasi-Static Brain Communication (BP-QBC) with the first device 102. The BP-QBC may be enabled by the wireless communication system 100 where a modulated electro-quasistatic signal is coupled to the internal tissue of the patient through a plurality of first device electrodes 112. The first device 102 may utilize dipole coupling to create an electric field between the plurality of first device electrodes 112. The second device 104 may be configured to be disposed substantially epicutaneously on the patient. The wireless BP-QBC from the first device 102 to the second device 104 may include an electrical uplink channel UL and the wireless BP-QBC from the second device 104 to the first device 102 includes an electrical downlink channel DL.

Figure 3:
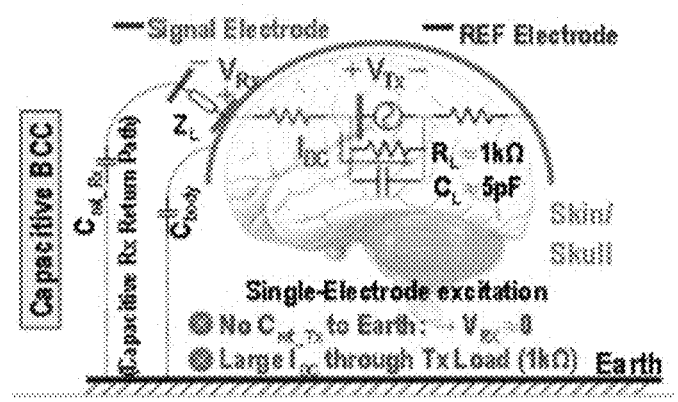
FIG. 3 is a schematic diagram, provided as prior art, that represents a traditional capacitive modality of body channel communication.
Figure 5:
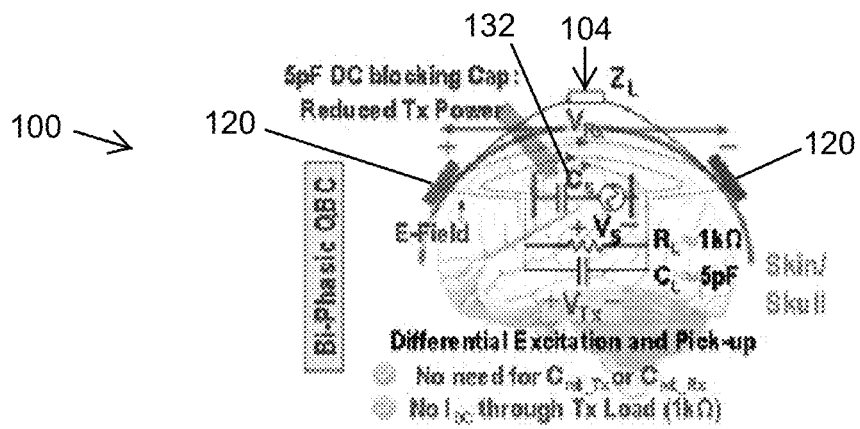
FIG. 5 is a schematic diagram depicting the wireless communication system utilizing a Bi-Phasic Quasi-Static Brain Communication modality of body channel communication, according to one embodiment of the present disclosure.
Figure 23:
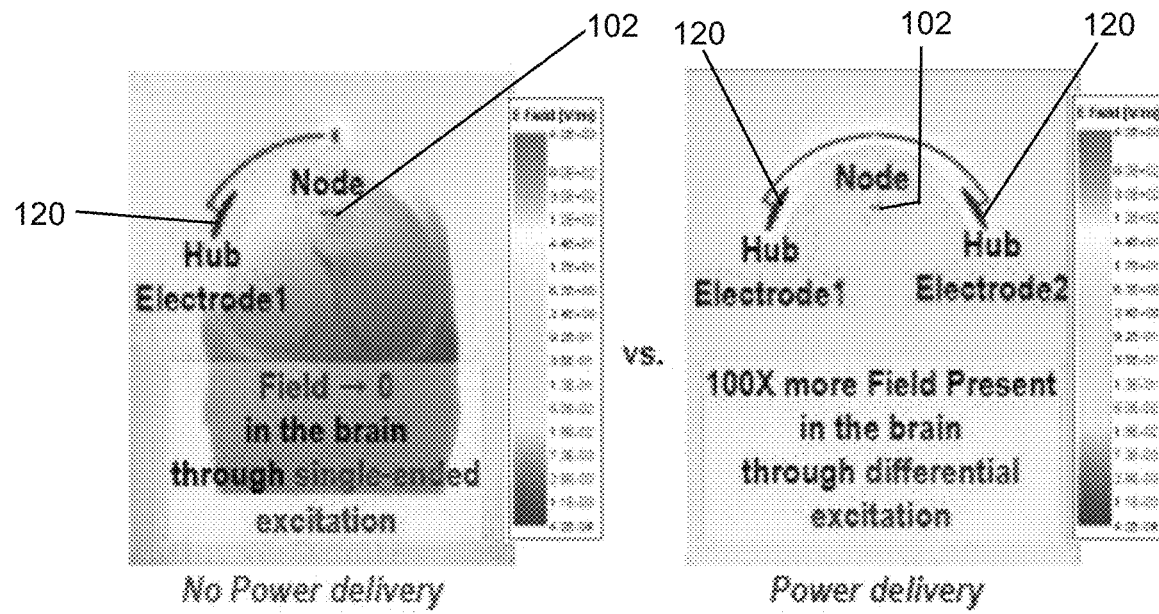
FIG. 23 is a first schematic diagram representing the lack of a field presence available through single-ended excitation in comparison to a second schematic diagram representing an available field presence through the use of differential excitation, according to one embodiment of the present disclosure.

In certain circumstances, the first device 102 may be a neural implant and the second device 104 may be a wearable headphone-shaped hub. The neural implant may more specifically include a polyimide flex board 122 and a system on a chip (SoC) 124. The first device electrode may include a signal electrode 126 and a reference electrode 128. In a specific example, the first device 102 may include a capacitor 130. In a specific example, the volume of the neural implant may be less than 5.75 mm$^3$ and the weight may be around 21 grams. As shown in FIGS. 5 and 23, the neural implant may be powered through external differential current excitations which is capable of producing more than 3.5 microwatts. With continued reference to FIG. 23, the use of differential excitation with a plurality of second device electrodes 120 for power delivery may advantageously provide up to a one-hundred-fold greater field presence in contrast to known single-ended excitation methods, such as capacitive body channel communication (BCC) as shown in FIG. 3.

Figure 6:
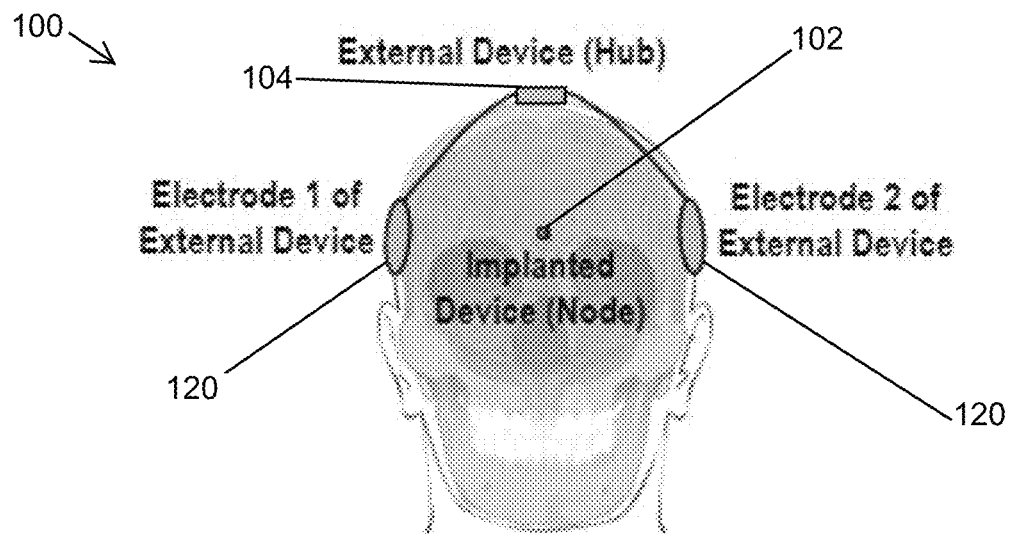
FIG. 6 is a front elevational view of the wireless communication system depicting the first device implanted in a tissue of a patient and a second device disposed on an exterior surface of the patient, according to one embodiment of the present disclosure.

As shown in FIG. 6, utilizing BP-QBC does not require any physical tethering or wiring from the second device 104 to the first device 102. Advantageously, the first device 102 may be more comfortably worn by the patient. Desirably, the first device 102 utilizing BP-QBC may also militate against the patient from undergoing surgery to remove or provide maintenance to the first device 102 due to the absence of wiring. Further, the quasi-static mode of signal transfer, through the use of BP-QBC, also enables a flat band transfer function w.r.t. frequencies, as well as enhanced physical security through lower leakage. The bi-phasic properties of utilizing BP-QBC may be understood as communication signals switching on both sides of a reference potential. In a specific example, the reference potential may include the first device 102 and the communication signals may be switched between a plurality of second device electrodes 120. The bi-phasic properties of the present disclosure may be understood to share similar characteristics to bi-phasic stimulation techniques which ensures that there is no ion-imbalance in the brain tissue.

Utilizing BP-QBC for communication in the first device 102 may permit the first device 102 to sense and transmit information to the second device 104 through the uplink channel UL. The second device 104 may send power and configuration/scan bits to the first device 102 through the downlink channel DL. Both the uplink channel UL and the downlink channel DL may use fully electrical signals to avoid transduction losses. Transduction loss should be understood as the energy loss from converting one form of energy to another. Known methods of wireless communication, such as Optical, Ultrasonic, and Magneto-Electric systems suffer from the aforementioned transduction losses and thereby require more energy than what is necessary in the present technology to make up for this loss. The uplink channel UL may use MHz-GHz narrow-band frequencies to avoid interfering with physiological signals and/or to avoid stimulating the brain tissue of the patient with low-frequencies. For traditional Galvanic body channel communication (G-BCC), the electrodes on the implant are shorted through the low-impedance (~kΩ) tissue/fluids in the body, resulting in high DC power consumption. A DC-blocking capacitor 132 in the signal path for BP-QBC creates a bi-phasic output that advantageously militates against the DC power going into the tissue of the patient and maintains ion balance.

Figure 28:
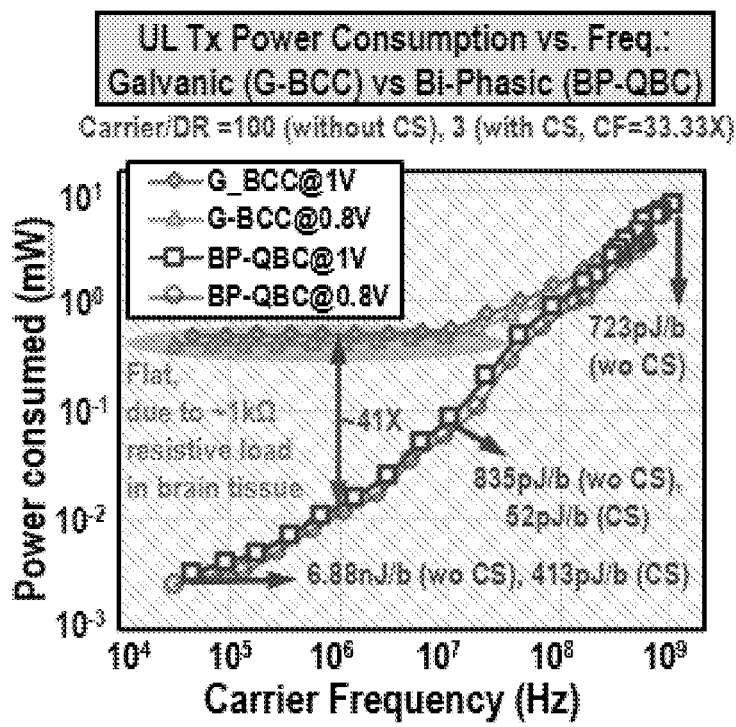
FIG. 28 is a line graph illustrating the lower uplink transfer power consumption of the Bi-Phasic Quasi-Static Brain Communication modality of body channel communication in comparison to the known galvanic modality of body channel communication.

The wireless communication system 100 may include certain ways to enhance energy efficiency. For instance, the wireless communication system 100 may use only electrical energy, so any transduction loss is greatly militated against or may even be eliminated. The wireless communication system 100 may include certain capabilities to enhance efficiency such as compressive sensing, collision avoidance, and duty cycling. In a specific example, the electrical downlink channel DL may utilize a transfer energy ranging from greater than zero microwatts up to about three microwatts. In a more specific example, the transfer energy of the downlink channel DL may range from about half of a microwatt to about one and a half microwatts. In a most specific example, the transfer energy of the downlink channel DL may be around 1.15 microwatts at ten megabits per second. As a whole, the wireless communication system 100 may require lower power in comparison to the known methods of brain-machine interfaces. As a non-limiting example, the wireless communication system 100 may be configured to exhibit an energy efficiency of fifty-two petajoule per bit (pJ/b), as shown in FIG. 28. Advantageously, the enhanced efficiency of the transfer energy of the downlink channel DL may permit the wireless communication system 100 to use megahertz and/or gigahertz narrow-band frequencies. Desirably, the downlink channel DL utilizing megahertz and/or gigahertz narrow-band frequencies may militate against interference with the psychological signals of the patient and may also militate against stimulating the brain tissue with low-frequencies. Further, the enhanced efficiency of the wireless communication system 100 may also enhance the amount and the speed of data that may be transferred between the first device 102 and the second device 104. For instance, the downlink channel DL may advantageously be configured to transmit data at 6 kbps to 10 Mbps.

Figure 34:
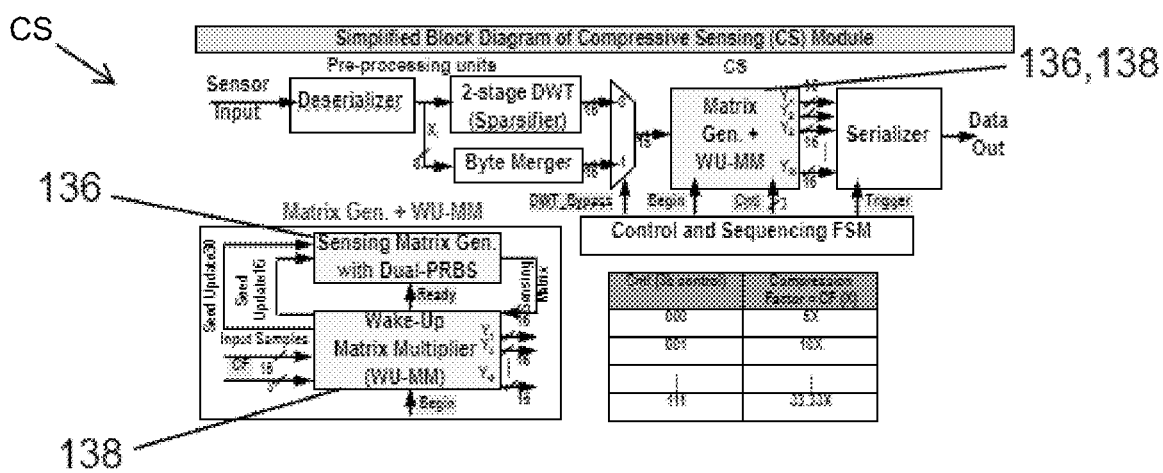
FIG. 34 is a schematic diagram illustrating a method of compressive sensing (CS) in the first device that compresses an input signal to the first device, according to one embodiment of the present disclosure.
Figure 35:
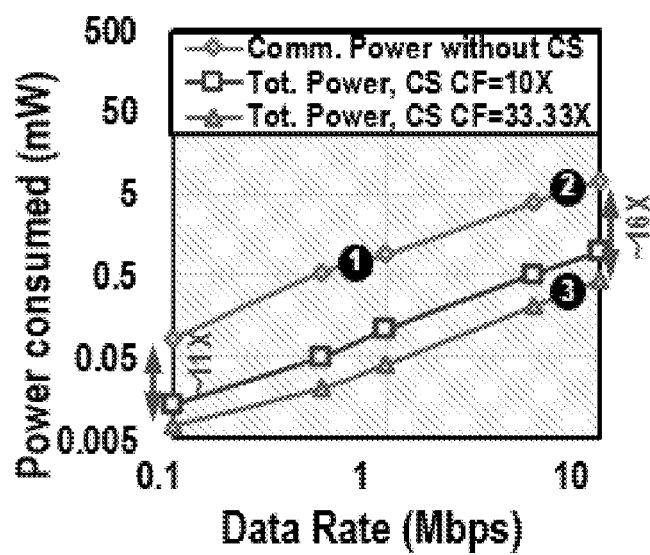
FIG. 35 is a line graph illustrating a lower power consumption of the wireless communication system utilizing compressive sensing, according to one embodiment of the present disclosure.
Figure 36:
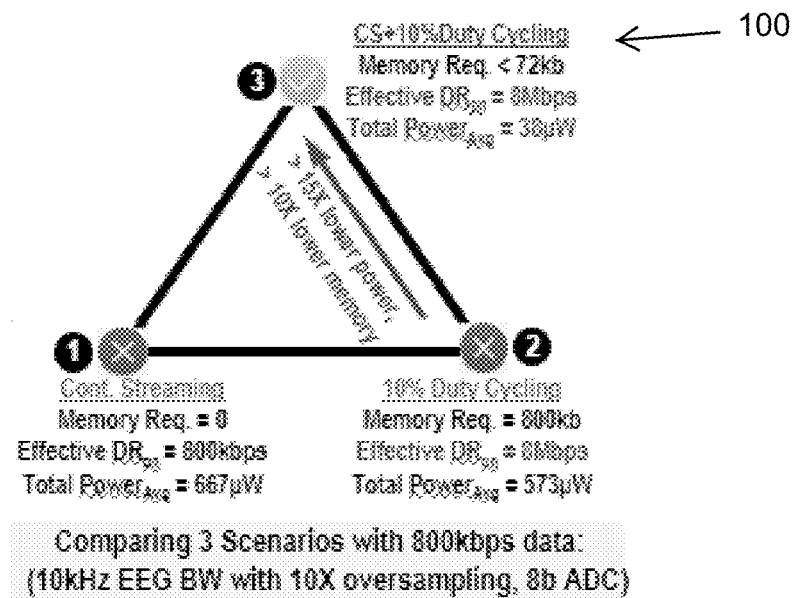
FIG. 36 is a schematic diagram illustrating the enhanced data rate and lower power consumption achieved when utilizing compressive sensing and duty cycling, according to one embodiment of the present disclosure.
Figure 44:
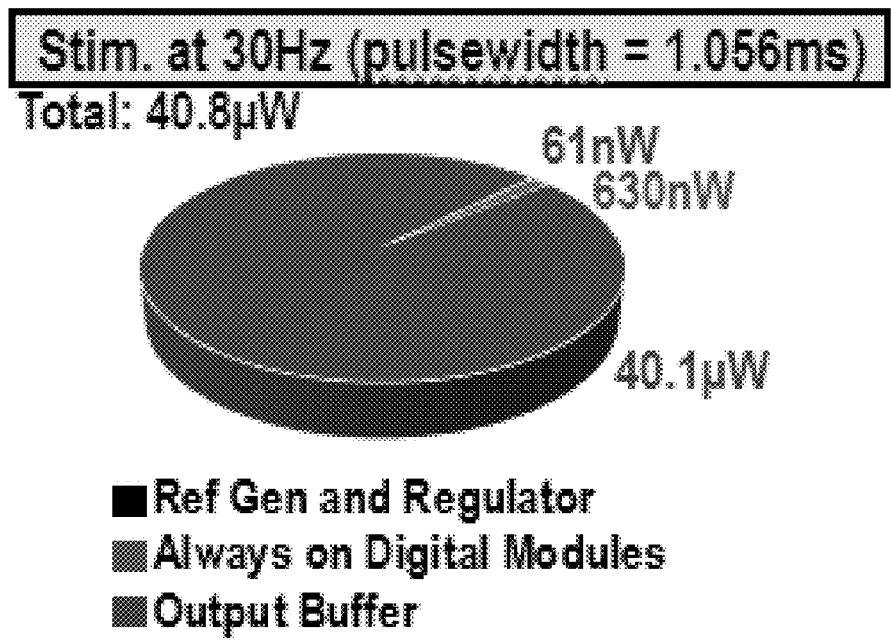
FIG. 44 is a pie chart illustrating the power consumption of the stimulator on the first device, according to one embodiment of the present disclosure.

The wireless communication system 100 may include ways of stimulating the neural environment of the patient. For instance, the first device 102 may include a stimulator 135 that is configured to provide compressive sensing capabilities. In a specific example, the stimulator 135 may be used to incite more neural activity from the patient. The stimulator 135 may be coupled to the first device data transmitter 106. The compressive sensing capabilities may also be provided with the use of duty cycled modules 136, 138 such as a duty cycled matrix generator 136 and a matrix multiplier 138 to compress the digital data. Advantageously, where the wireless communication system 100 includes the compressive sensing capabilities, the volume of data to be communicated may be reduced. As a non-limiting example, the digital data signal may be compressed by a factor ranging from one-fold up to around thirty-two-fold. In a specific example, as shown in FIGS. 34-36, where the wireless communication system 100 includes a data rate of around eight megabytes per second, the wireless communication system 100 may have around a sixteen-fold enhancement in power efficiency. In another specific example, the stimulator 135 may have a maximum stimulation power of around 1.2 megawatts and the stimulator 135 may have a stimulation efficiency of around 89.2%. In a non-limiting example, as shown in FIG. 44, the stimulator 135 may be configured to consume around forty microwatts at thirty hertz. One skilled in the art may select other suitable methods of stimulating the neural environment of the patient and providing compressive sensing capabilities, within the scope of the present disclosure.

Figures 16, 17:
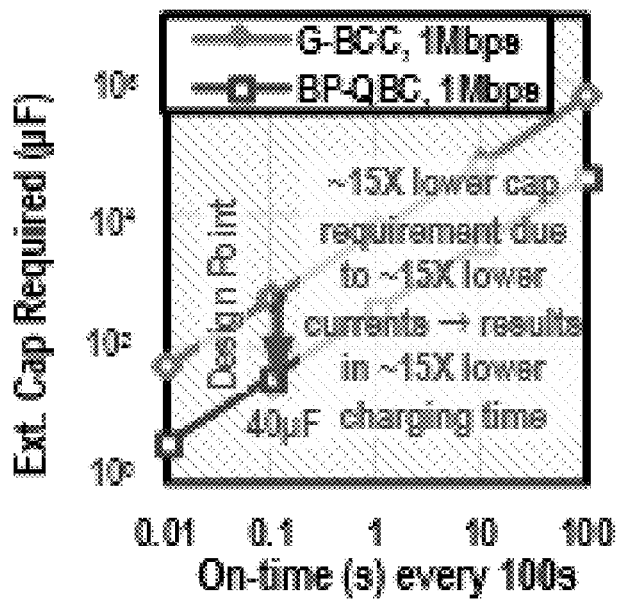
FIG. 16 is a line graph illustrating the possible reduction in charging time of the present technology utilizing Bi-Phasic Quasi-Static Brain Communication modality of body channel communication in comparison to the known galvanic modality of body channel communication, according to one embodiment of the present disclosure.
FIG. 17 is a schematic diagram illustrating a representation of the charge pump, according to one embodiment of the present disclosure.
Figure 18:
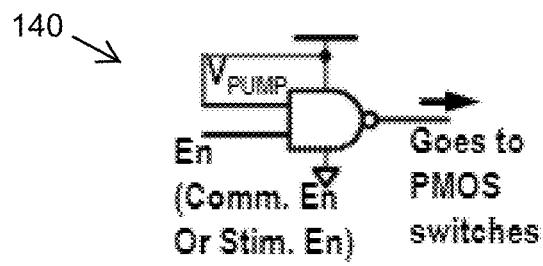
FIG. 18 is a schematic diagram illustrating a partial representation of a specific non-limiting application of the charge pump, further depicting a leakage reduction technique in a power-gating switch, according to one embodiment of the present disclosure.
Figure 19:
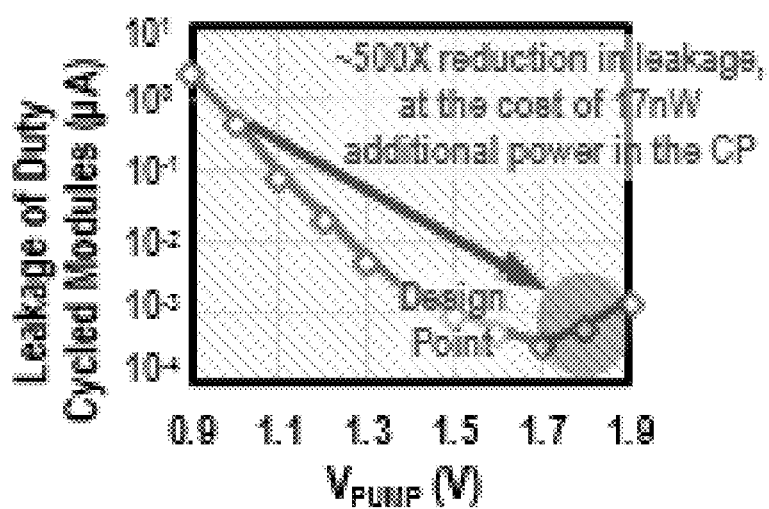
FIG. 19 is a line graph illustrating the reduction of leakage from the duty cycled modules with the use of the charge pump, according to one embodiment of the present disclosure.

In certain circumstances, as shown in FIG. 18, the first device 102 may include a power-gating switch 140. The power gating switch 140 may be configured to reduce the average power consumption of the first device 102 by turning off the first device data transmitter 106 when the first device data transmitter 106 is not in use. However, even in off state, there is significant leakage of energy in the power-gated circuits. In a specific example, this significant leakage may be a loss of around one microwatt. To militate against this leakage, the wireless communication system 100 may further include a charge pump 142, as shown in FIG. 17, that is coupled to the first device 102. The charge pump 142 may be configured to militate against leakage of the duty cycled modules 136, 138 and the power-gated circuits in the first device 102. As shown in FIG. 19, the charge pump 142 may advantageously reduce the energy leakage of the duty cycled modules 136, 138 by around five-hundred-fold at the cost of only about seventeen nanowatts. A skilled artisan may select other suitable methods of reducing energy leakage, within the scope of the present disclosure.

Figure 20:
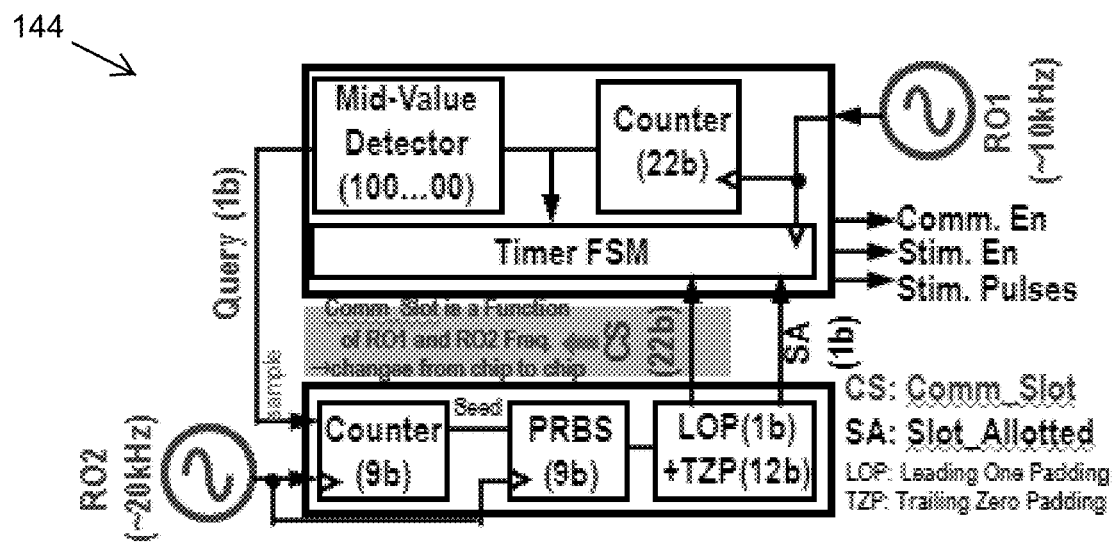
FIG. 20 is a schematic diagram illustrating a representation of the randomizer, further depicting the randomizer as a ring-oscillator based physical unclonable function circuit that may be configured to provide a collision avoidance feature, according to one embodiment of the present disclosure.

In certain circumstances, the first device 102 may include a collision avoidance capability. The collision avoidance capability may be enabled by a ring-oscillator based physical unclonable function circuit 144, as shown in FIG. 20. It should be appreciated that the collision avoidance capability may permit the first device 102 to transmit modulated electro-quasi-static signals at designated time slots. In certain circumstances, the wireless communication system 100 may include a randomizer 146 and/or a timer 148. The randomizer 146 and/or the timer 148 may be coupled to the first device 102. The randomizer 146 and/or the timer 148 may be configured to cooperatively provide the collision avoidance feature. Advantageously, the collision avoidance capability may enhance the communication between the first device 102 and the second device 104 where the first device 102 includes more than one implant disposed within the patient. For instance, the collision avoidance capability may militate against the wireless communication system 100 from incorrectly recognizing a signal coming from a different implant than what the signal actually came from, where the first device 102 includes a plurality of implants. One skilled in the art may select other suitable methods of providing the collision avoidance capability, within the scope of the present disclosure.

Figure 4:
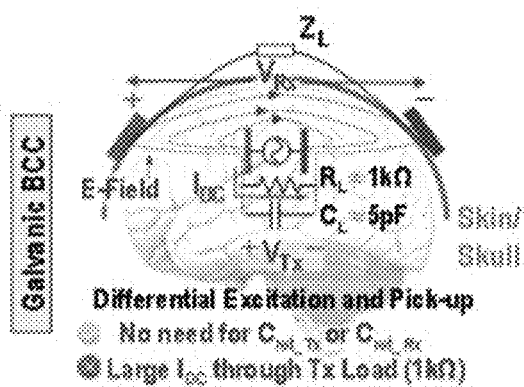
FIG. 4 is a schematic diagram, provided as prior art, that represents a galvanic modality of body channel communication.

The wireless communication system 100 may include ways to militate against a DC current path from traveling through the patient. For instance, as shown in FIG. 5, the wireless communication system 100 may include a DC blocking capacitor 132 coupled to the first device data transmitter 106. The DC blocking capacitor 132 may block the DC current to desirably minimize power transferred through the brain tissue of the patient. For instance, the present technology may be configured to operate at a carrier frequency of around one megahertz where the DC blocking cap is used. For reference, known methods of Galvanic BCC, as shown in FIG. 4, operate at a carrier frequency of 10 megahertz which undesirably requires around six times more power.

In certain circumstances, the wireless communication system 100 may include ways to enhance a range between the first device 102 and the second device 104, where the first device 102 is disposed in the brain of a patient. For instance, the wireless communication system 100 may be configured to operate efficiently up to a predetermined distance between the first device 102 and the second device 104, or otherwise known as a channel length CL. In a specific example, the channel length CL may be up to about fifty-five millimeters. In more specific example, the wireless communication system 100 may include an end-to-end loss of about sixty decibels where the channel length CL is fifty-five millimeters and where the first device 102 is implanted in the brain of a patient. Advantageously, the sixty-decibel end-to-end loss of the wireless communication system 100 presents an enhancement over the known methods such as optical, ultra-sonic, magnetic-electric, and inductive transference methods, where each method has an end-to-end loss greater than eighty decibels. In comparison to other known methods of body channel communication (BCC) modalities, the present technology enhances a receiver signal strength and minimizes the required transmission power. For instance, the present technology greatly enhances the receiver signal strength over capacitive BCC. Further, the present technology drastically reduces the required power for signal transmission over both capacitive BCC and galvanic BCC. More specifically, the present technology reduces the required power for signal transmission by around forty-one-fold over galvanic BCC. Desirably, the greater channel length CL capacity with minimized end-to-end loss permits the wireless communication system 100 to require less energy to transfer data between the first device 102 and the second device 104. Further, as shown in FIG. 16, the charging time of the present technology utilizing BP-QBC modality of body channel communication may advantageously reduce the charging time of the first device 102 by around fifteen-fold in comparison to the known galvanic modality of body channel communication.

Figure 8:
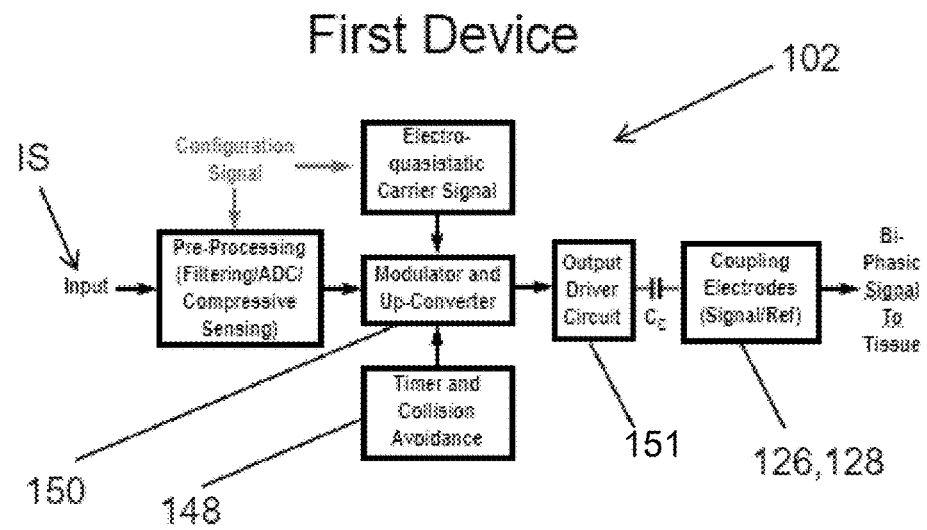
FIG. 8 is a flow diagram illustrating a method for using the first device of the wireless communication system, according to one embodiment of the present disclosure.
Figure 11:
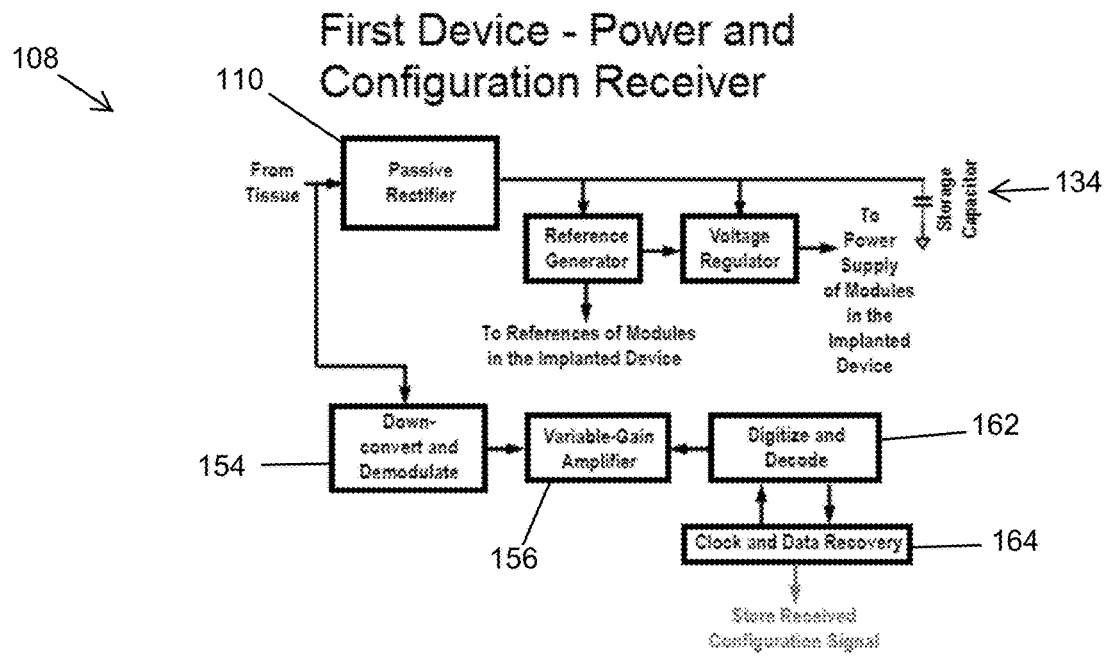
FIG. 11 is a flow diagram illustrating a method for using a Power and Configuration Receiver of the first device, according to one embodiment of the present disclosure.
Figure 13:
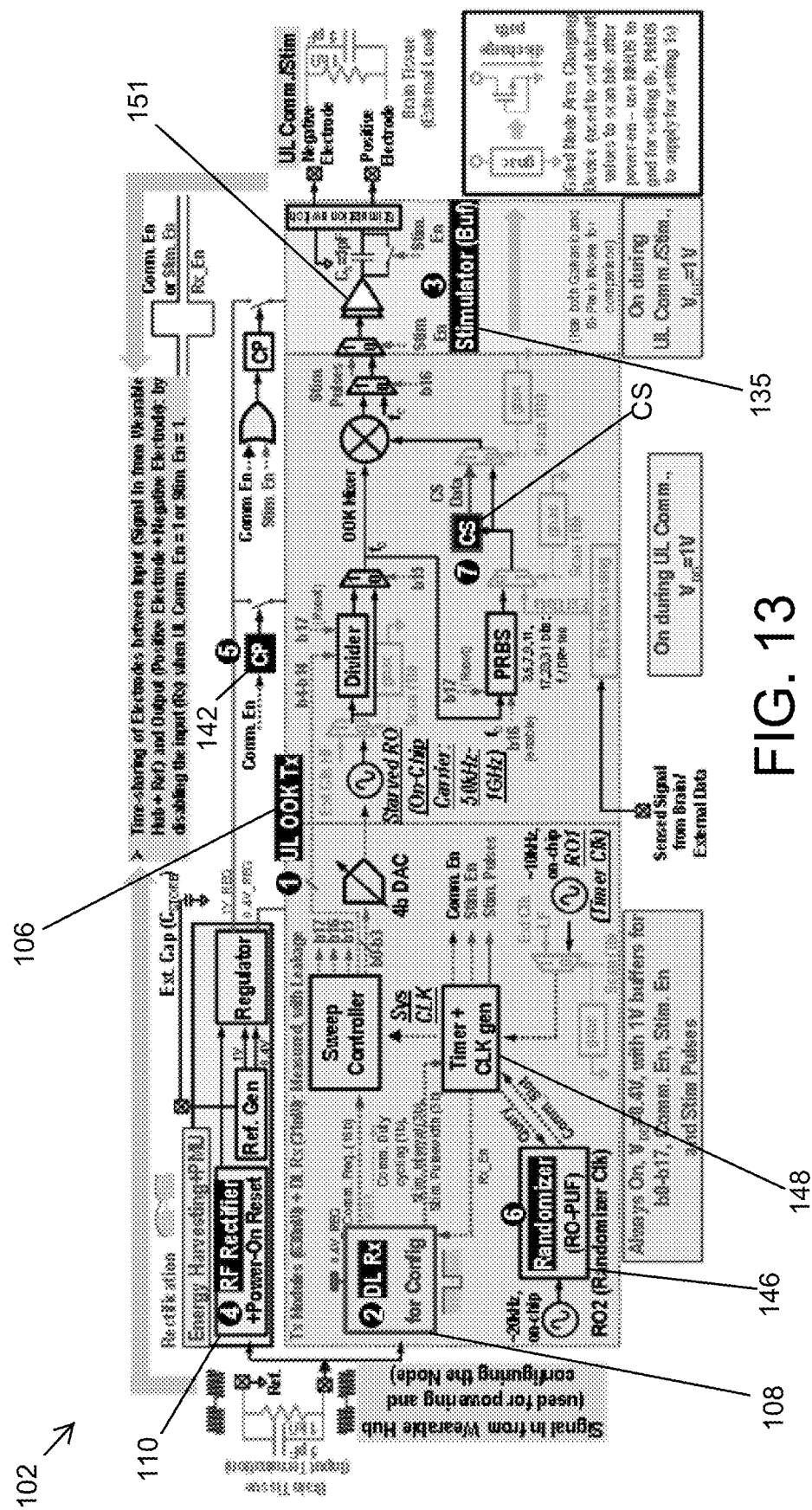
FIG. 13 is a schematic diagram illustrating a non-limiting example of the first device, further depicting an uplink transmitter, a downlink receiver, a stimulator, an energy harvester, a charge pump, a randomizer, and a compressive sensing unit, according to one embodiment of the present disclosure.
Figure 26:
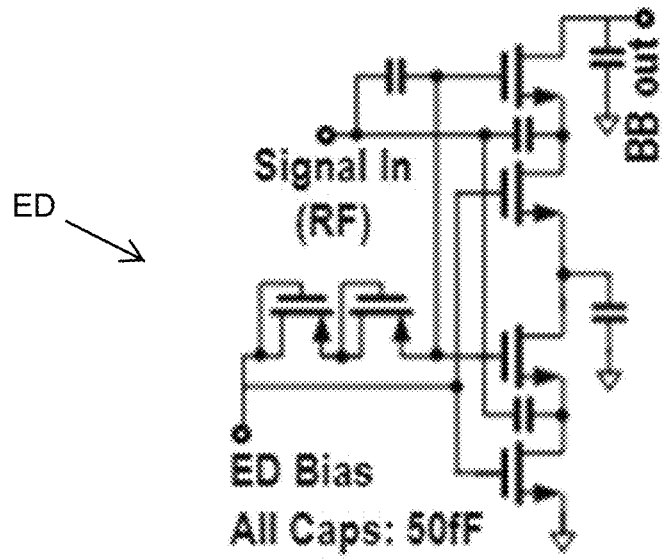
FIG. 26 is a schematic diagram illustrating a representation of a Passive Envelope Detector (ED), according to one embodiment of the present disclosure.
Figure 27:
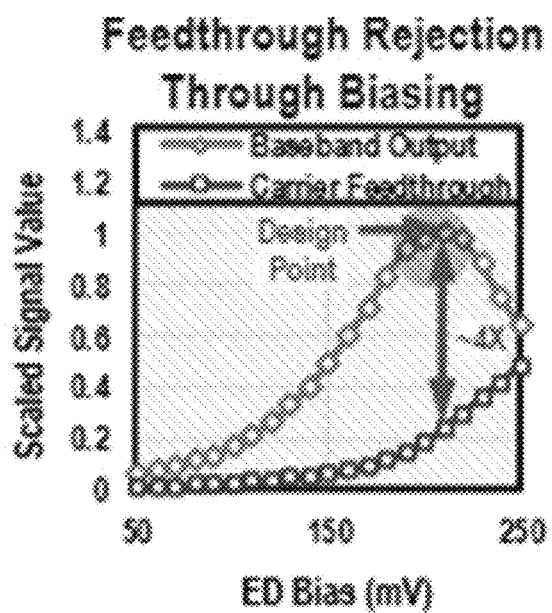
FIG. 27 is a line graph illustrating a method of selecting a bias/control voltage of the ED, as shown in FIG. 26, according to one embodiment of the present disclosure.

In certain circumstances, as shown in FIGS. 8, 11 and 13, the first device data receiver 108 may include various components and have certain functions. As a non-limiting example, the first device data receiver 108 may include a passive envelope detector ED, as shown in FIG. 26. The passive envelope detector ED may advantageously detect data without requiring additional active devices and/or transistors. As shown in FIG. 27, the passive envelope detector ED may select a bias/control voltage. The desired output of the passive envelope detector ED may first increase and then decrease as the bias voltage of the passive envelope detector ED is increased. During which, an undesired component called a carrier feedthrough may continue to increase with the increase in the bias voltage. As shown in FIG. 27, a design philosophy is to maximize the desired output of the passive envelope detector ED by controlling the bias voltage, while the carrier feedthrough is around four-fold lower. One skilled in the art may select other suitable methods of detecting data and lowering carrier feedthrough, within the scope of the present disclosure.

Figure 46:
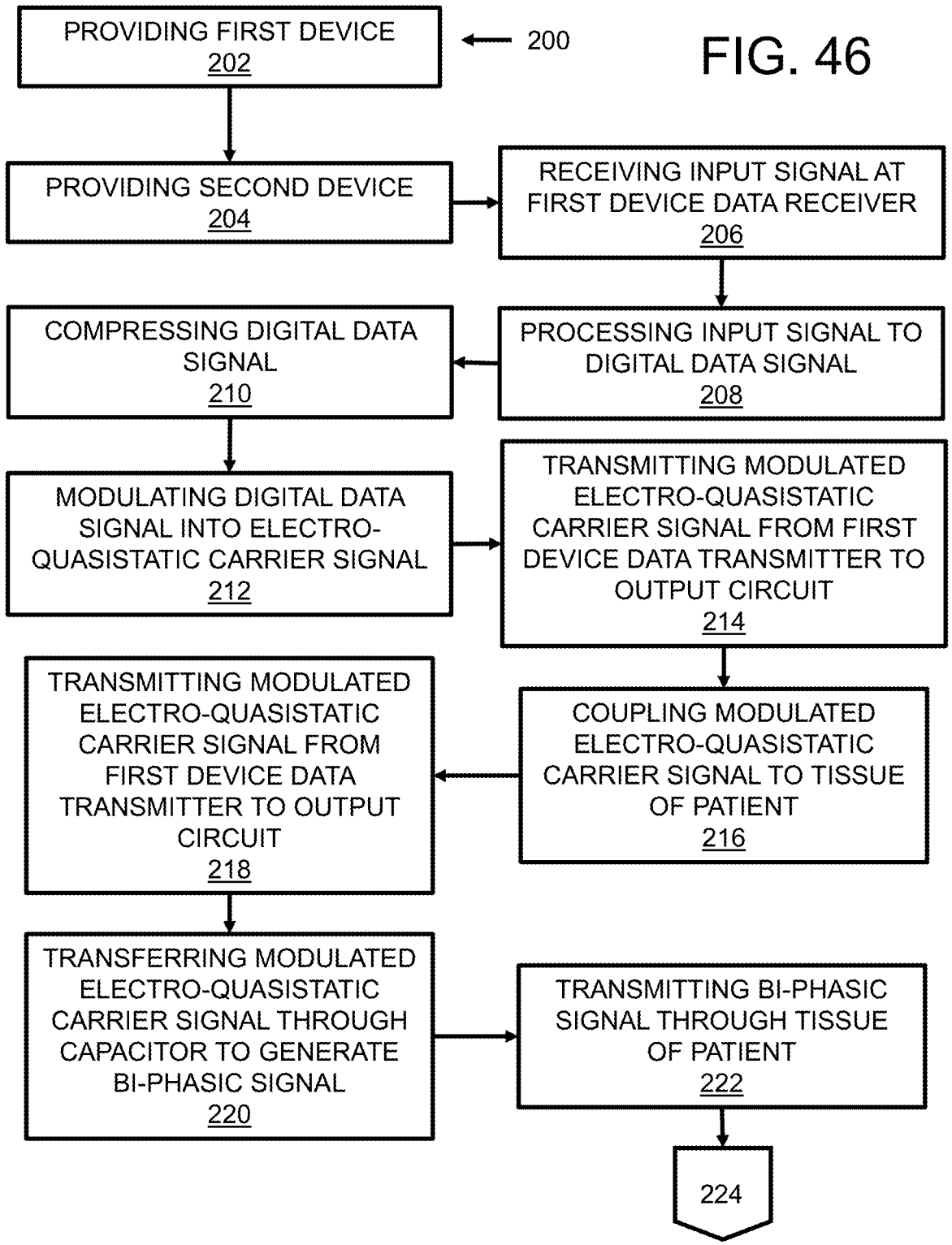
FIG. 46 is a flowchart of a first method for using the wireless communication system, according to one embodiment of the present disclosure.
Figure 47:
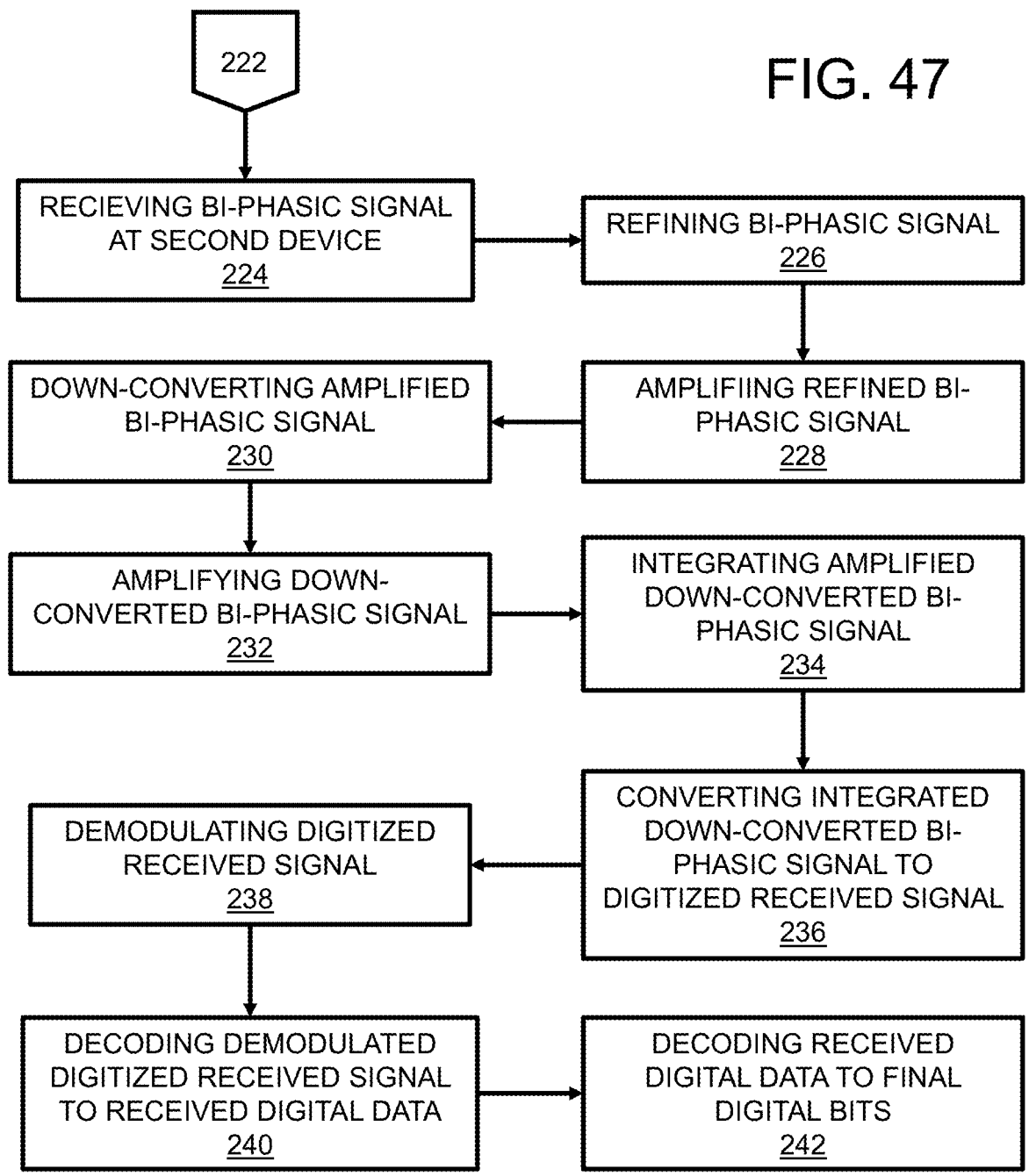
FIG. 47 is a continuation of the flowchart as shown in FIG. 46, further depicting the use the wireless communication system.

As shown in FIGS. 46-47, the present technology may include various methods of using the wireless communication system 100 through a tissue of a patient. For instance, a first method 200 of using the wireless communication system 100 may include providing a first device 102 including a first device data transmitter 106, a first device data receiver 108, an energy harvester 110, a first device electrode 112, and a capacitor 130 electrically coupled to the first device electrode 112. The first device data transmitter 106 may include a modulator 150. The first device 102 may be configured to be substantially implanted within the patient. The first method may also include providing a second device 104 including a second device data receiver 114, a second device data transmitter 116, and a power transmitter 118. The second device 104 may be configured to communicate via wireless BP-QBC with the first device 102. The second device 104 may be configured to be disposed substantially epicutaneously on the patient. The wireless communication from the first device 102 to the second device 104 may include an electrical uplink channel UL. The wireless communication from the second device 104 to the first device 102 may include an electrical downlink channel DL.

Next, as shown in FIG. 8 and FIG. 46, the first method 200 may include receiving an input signal IS at the first device 102. In a specific example, the input signal IS may include an input configuration signal received at the first device data receiver 108. In another specific example, the input signal IS may include a biological signal received at the first device electrode(s) 112. at the first device data receiver 108. The first device data receiver 108 may also be known as the downlink receiver. The input signal IS may be received through a sensing port (not shown) of the first device 102. As non-limiting examples, the input signal IS may include a physiological signal, an analog electrical signal, a digital electrical signal, and/or an activation signal. The input signal IS may be processed into a digital data signal at the first device data transmitter 106. In a specific example, the input signal IS may be processed into a digital data signal by a transmitter logic circuit (not shown) of the first device data transmitter 106.

Figure 12:
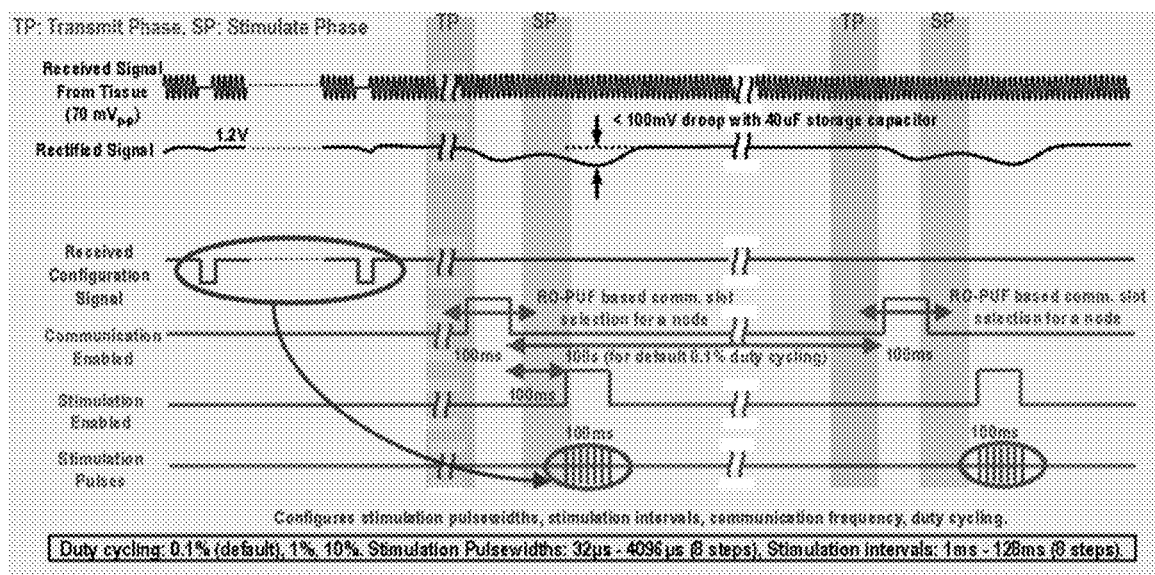
FIG. 12 is a timing diagram illustrating a non-limiting example of a transmit phase and a stimulate phase that may be selected to provide a duty-cycling function, according to one embodiment of the present disclosure.

In certain circumstances, the digital data signal may then be compressed. The digital data signal may be compressed by selectively sparsifying the digital data signal through a logic circuit capable of performing a discrete wavelet transform. In other words, the wireless communication system 100 may identify and extract the important sections of code from the digital data signal which may advantageously minimize the size of the data signal to be transmitted. The digital data signal may also or alternatively be compressed by utilizing a duty cycled matrix generator 136 with a matrix multiplier 138 to compress the digital data. More specifically, as shown in FIG. 12, the duty cycled matrix multiplier 138 may be configured to provide a transmit phase TP and a stimulate phase SP that may be selected to advantageously provide a duty-cycling function to compress the digital data signal.

With continued reference to FIG. 46, the digital data signal may then be modulated into an electro-quasistatic carrier signal. In a specific example, the modulator 150 may be coupled to the first device data transmitter 106. In a more specific example, the modulator 150 may include one or more of a pulse-width modulator circuit (not shown), a pulse-position modulation circuit (not shown), a pulse frequency modulation circuit (not shown), a pulse amplitude modulation circuit (not shown), a quadratic amplitude modulator circuit (not shown), and an electro-quasi-static carrier generation circuit (not shown) with On-Off Keying. The electro-quasistatic carrier signal may include a frequency ranging from fifty kilohertz (kHz) to thirty megahertz (MHz).

Afterwards, the modulated electro-quasistatic carrier signal may be transmitted from the first device data transmitter 106 to an output driver circuit 151. Then, the modulated electro-quasistatic carrier signal may be coupled to the tissue of the patient through the first device electrode 112. In a specific example, the first device electrode 112 may include a plurality of electrodes and at least one of the electrodes may be coupled in series to the capacitor 130. The modulated electro-quasistatic signal may be coupled to the tissue of the patient through at least two of the first electrodes 112 and the capacitor 130, thereby enabling bi-phasic electro-quasi-static communication. It should be appreciated that more than one capacitor 130 may be used with the first device 102. The modulated electro-quasistatic carrier signal may then be transferred through the capacitor 130 to generate a bi-phasic signal. The bi-phasic signal may be transmitted through the tissue of the patient where the bi-phasic signal may be received by the second device 104, as shown in FIGS. 46-47. More specifically, the bi-phasic signal may be received by the second device electrode 120 that is coupled to the second device 104. Advantageously, the first method 200 of using the wireless communication system 100 may maintain a completely electrical modality for the transmitted bi-phasic signal from the first device 102 to the second device 104.

In certain circumstances, the first method 200 may further include transmitting the signal through dipole coupling. The first method 200 may also include blocking the DC current path through the patient. In certain circumstances, the first method 200 may include transmitting the modulated electro-quasistatic signal at a designated time slot, thereby incorporating a collision avoidance feature. The designated time slot may be implemented using a ring-oscillator based physical unclonable function circuit 144. The ring-oscillator based physical unclonable function circuit 144 may be configured designate a time slot for a particular transmitter of the first device 102.

In certain circumstances, the second device 104 may use a galvanic mode of signal reception using at least two second device electrodes 120 to receive the bi-phasic signal. Alternatively, the second device 104 may use a capacitive mode of signal reception using at least one second device electrode 120 to receive the bi-phasic signal.

Figure 9:
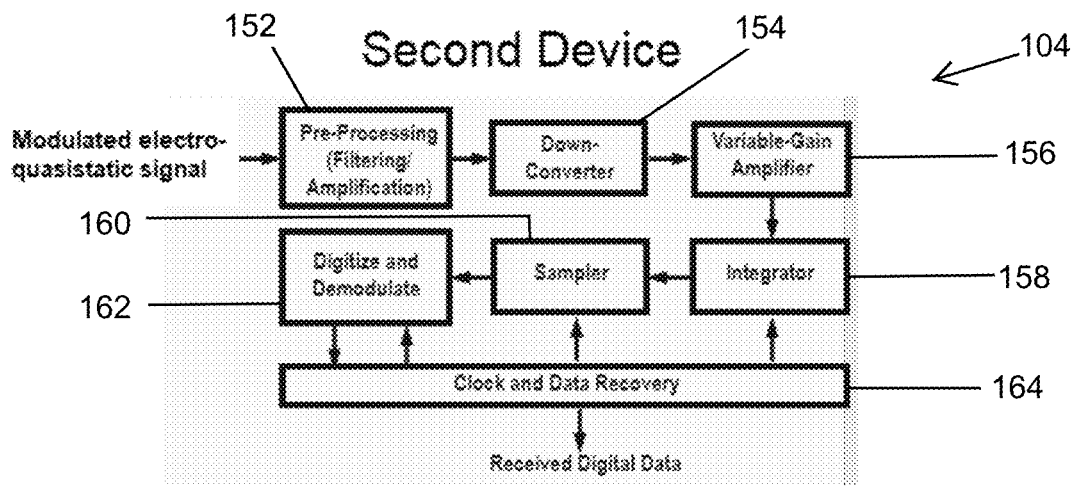
FIG. 9 is a flow diagram illustrating a method for using the second device of the wireless communication system, according to one embodiment of the present disclosure.

In certain circumstances, the second device 104 may be used in various ways. As shown in FIG. 47, as a continuation to the first method 200 of using the wireless communication system 100 shown in FIGS. 9 and 46, the first method 200 may include removing and/or filtering interferences from the bi-phasic using a pre-processing unit 152, thereby producing a refined bi-phasic signal. The refined bi-phasic signal may be selectively amplified by using the pre-processing unit 140 that may include a variable-gain low-noise amplifier, thereby generating a selectively amplified bi-phasic signal. Then, the selectively amplified bi-phasic signal may be down-converted using a down-converter 154 to generate a down-converted bi-phasic signal. The down-converted bi-phasic signal may then be selectively amplified using a variable-gain amplifier 156 to generate a selectively amplified down-converted bi-phasic signal. Afterwards, the selectively amplified down-converted bi-phasic signal may be integrated using an integrator 158 thereby creating an integrated down-converted bi-phasic signal. The integrated down-converted bi-phasic signal may then be converted into a digitized received signal. This conversion may include sampling the integrated down-converted bi-phasic signal using a sampler 160 that is coupled to the second device 104. The sampling thereby generates a sampled integrated down-converted bi-phasic signal that may then be digitized using an analog to digital converter (not shown) that is coupled to the second device 104. The digitized received signal may be demodulated and decoded using a decoding logic circuit 162, thereby generating a received digital data. More specifically, the digital data may be retrieved using a digital demodulation circuit (not shown) that may be included in the decoding logic circuit 162. The decoding logic circuit 162 may further utilize a clock and data recovery circuit 164 that may be used to synchronize the received digital data to recover the timing information of the first device data transmitter 106. The synchronized received digital data may then be decoded to generate final digital bits using the decoding logic circuit 162.

Figure 10:
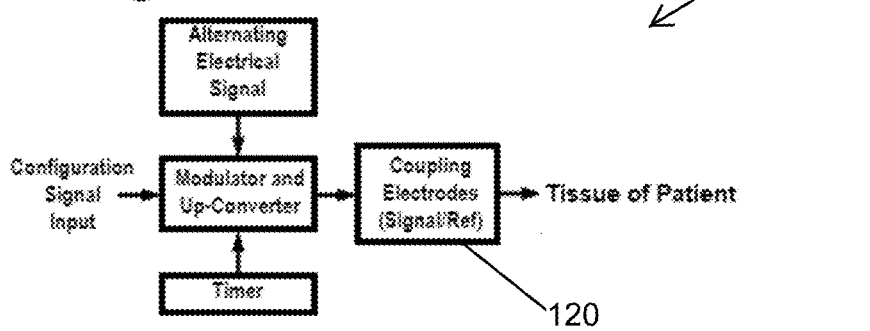
FIG. 10 is a flow diagram illustrating a method for using an External Power and Configuration Transmitter of the second device, according to one embodiment of the present disclosure.
Figure 25:
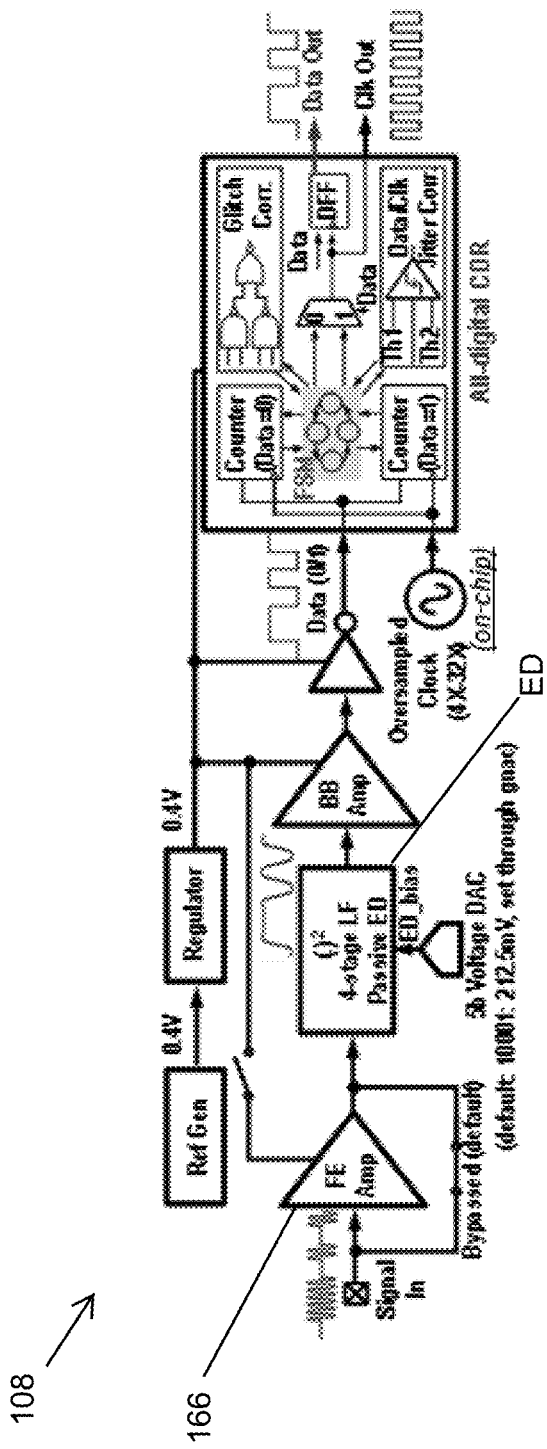
FIG. 25 is a schematic diagram illustrating a representation of the Power and Configuration Receiver of the first device, according to one embodiment of the present disclosure.
Figure 48:
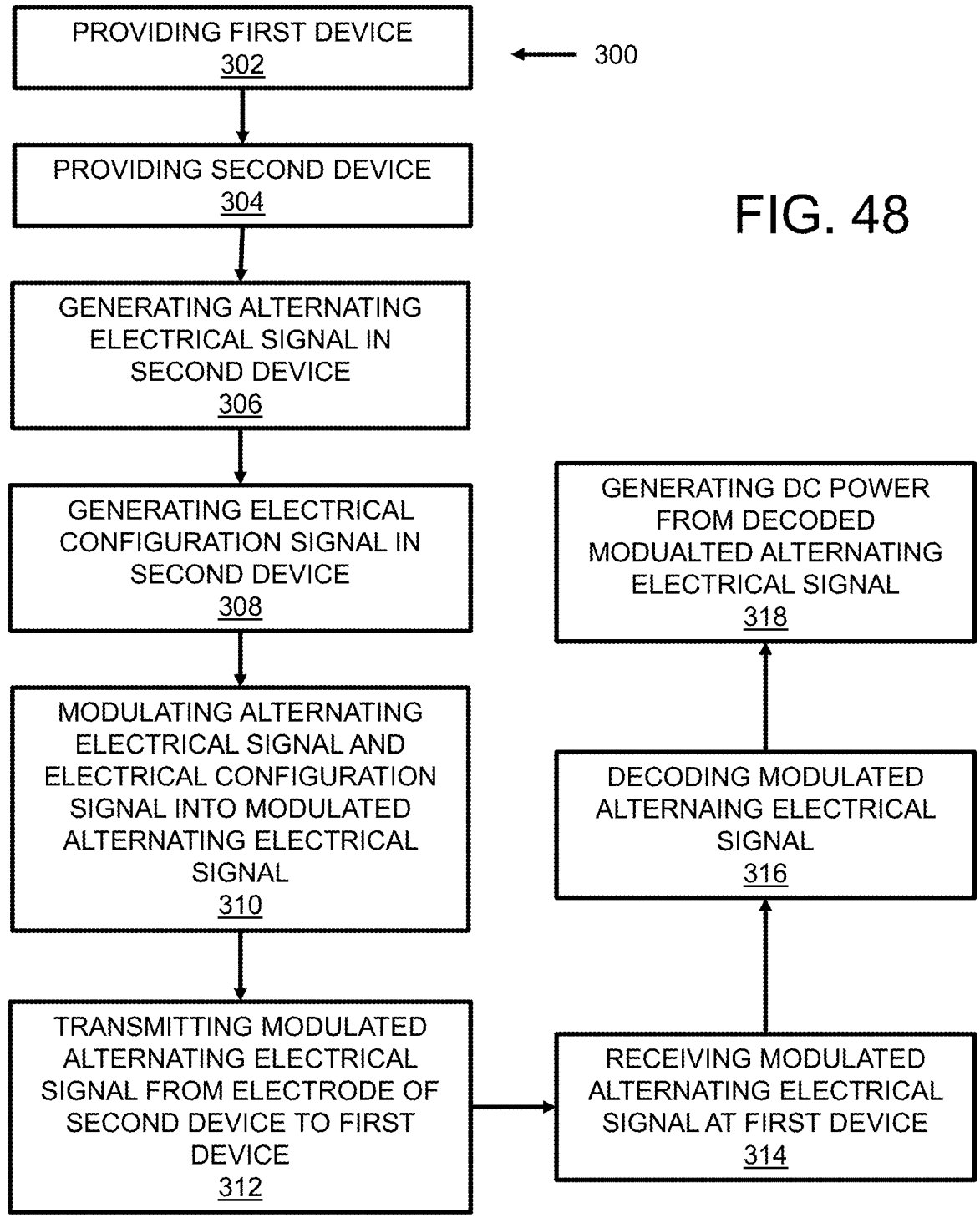
FIG. 48 is a flowchart of a second method for using the wireless communication system, according to one embodiment of the present disclosure.

In certain circumstances, the method of using the wireless communication system 100 may include various ways of transmitting power from the second device 104 to the first device 102. For instance, as shown in FIG. 48, a second method 300 of using the wireless communication system 100 may include generating an alternating electrical signal in the power and configuration transmitter 116, 118 of the second device 104, as shown in FIG. 25. Next, an electrical configuration signal may also be generated in the power and configuration transmitter 116, 118 of the second device 104. In a specific example, the generation of the electrical configuration signal may include combining a plurality of signals. For instance, the electrical configuration signal may include the combination of a first electrical configuration signal that is configured to designate a frequency of an electro-quasistatic carrier signal to be used in the first device 102, a second electrical configuration signal to designate a compression factor to be used in the first device 102, and a third electrical configuration signal to designate a pulse-width and a pulse-frequency to be used in the implanted stimulator 135 of the first device 102. As shown in FIGS. 10 and 48, the alternating electrical signal and the electrical configuration signal may be modulated in the power and configuration transmitter 116, 118 of the second device 104, thereby creating a modulated alternating electrical signal. The modulated alternating electrical signal may be transmitted from the second device electrode 120. In a specific example, the modulated alternating electrical signal may be transmitted from a plurality of coupled second device electrodes 120. The modulated alternating electrical signal may be transmitted through the tissue of the patient to the first device 102. In a more specific example, the modulated alternating electrical signal may be coupled to the tissue of the patient using two or more second device electrodes 120 through the BP-QBC mode of power transfer, which advantageously maintains a fully electric modality for transmitting the modulated alternating electrical signal from the second device 104 to the first device 102. The modulated alternating electrical signal may then be received by the first device 102. Afterwards, the electrical configuration signal from the modulated alternating electrical signal may be decoded in the first device 102. Then, the first device 102 may generate DC power from the modulated alternating electrical signal.

Figure 14:
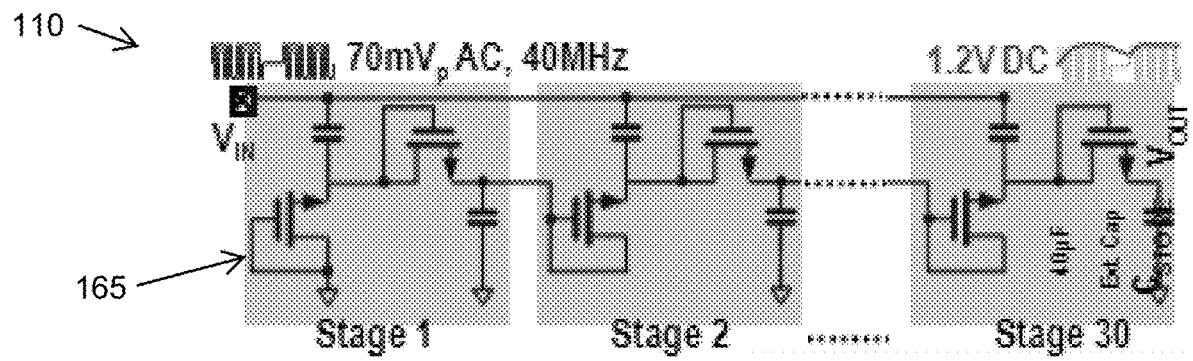
FIG. 14 is a schematic diagram illustrating a partial representation of the energy harvester particularly being depicted as a thirty-stage radio-frequency rectifier with one external cap according to one embodiment of the present disclosure.
Figure 15:
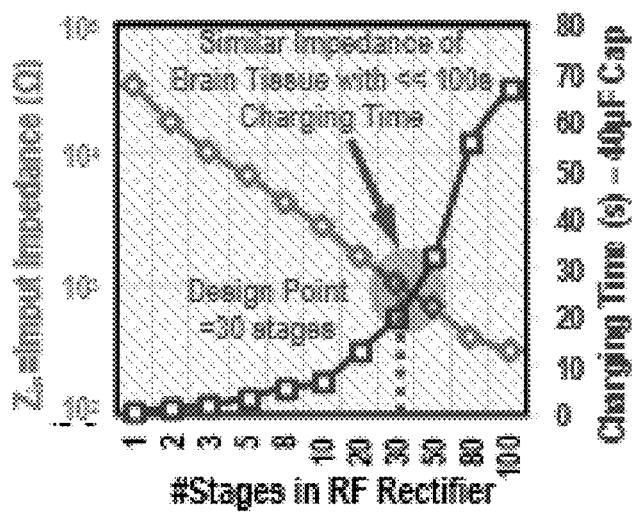
FIG. 15 is a line graph illustrating the relation between input impedance and charging time showing an ideal configuration of the radio-frequency rectifier to include about thirty stages, according to one embodiment of the present disclosure.
Figure 45:
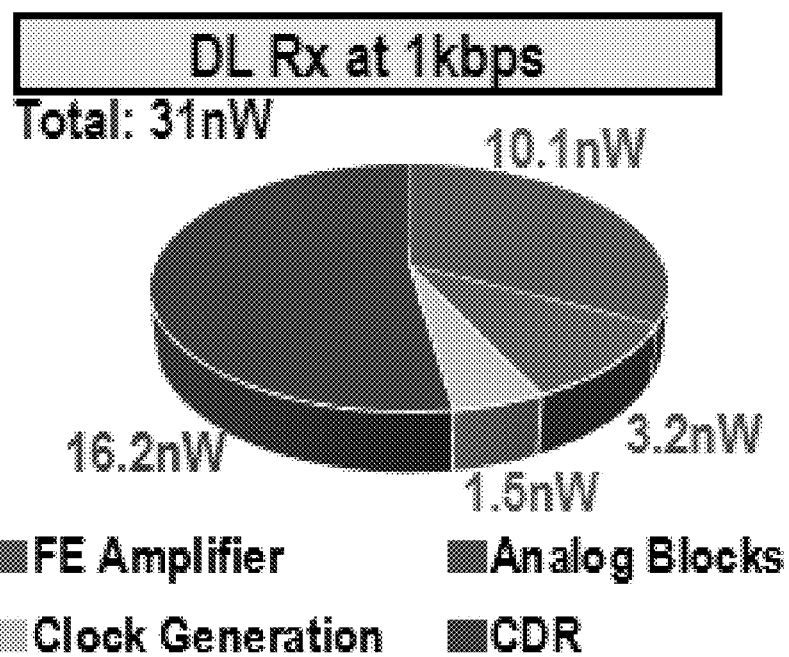
FIG. 45 is a pie chart illustrating the power consumption of the downlink receiver on the first device, according to one embodiment of the present disclosure.

In certain circumstances, the first device 102 may convert the modulated alternating electrical signal to a DC signal using the energy harvester 110, as shown in FIG. 11. In a specific example, the energy harvester 110 may include a passive rectifier circuit. In a more specific example, as shown in FIG. 14, the passive rectifier circuit may include a thirty-stage radio-frequency rectifier with one external cap. As shown in FIG. 15, a relation between input impedance and charging time showed an ideal configuration of the radio-frequency rectifier to include about thirty stages. In another specific example, as shown in FIG. 14, the modulated alternating electrical signal may be converted to the DC signal using a diode-connected metal-oxide-semiconductor field-effect transistor (MOSFET) 165. Other methods of converting the modulated alternating electrical signal to the DC signal may include the use of diodes. Advantageously, the use of a diode-connected MOSFET 165 may reduce the area and/or footprint on the first device 102. Desirably, the diode-connected MOSFET 165 may be more easily integrated onto the first device 102. The electrical energy from the modulated alternating electrical signal may be harvested onto the capacitor 134. The harvested energy may be used in various manners. Non-limiting examples of the various uses of the harvested energy may include down-converting and demodulating the modulated alternating electrical signal, selectively amplifying the demodulated electrical configuration signal, converting the selectively amplified demodulated electrical configuration signal into the digitized configuration signal, decoding and storing the digitized configuration signal, storing the received electrical configuration signal in an on-chip memory, and synchronizing the received electrical configuration signal with a clock and data recovery circuit 164 to recover the timing information of the power and configuration transmitter from the second device 104. As a non-limiting example, the first device data receiver 108 may use only around thirty-one nanowatts at a data rate of one kilobit per second, as shown in FIG. 45.

Figure 49:
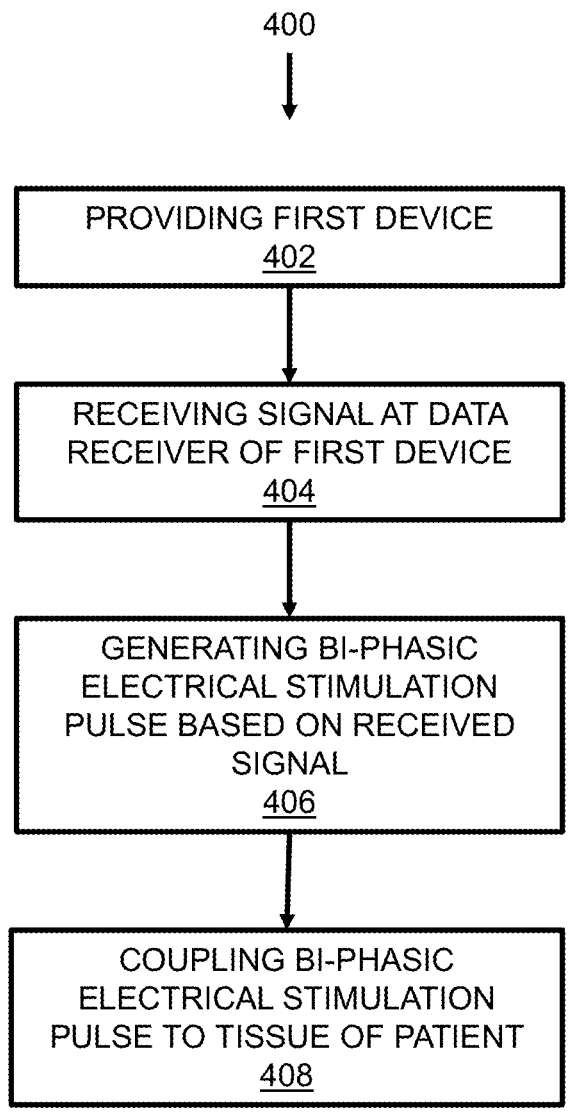
FIG. 49 is a flowchart of a third method for using the wireless communication system, according to one embodiment of the present disclosure.

In certain circumstances, the first device 102 may be used according to various other methods. As shown in FIG. 49, a third method 400 may include providing a first device 102 having a first device data receiver 108, a first device electrode 112, and a stimulator 135. The stimulator 135 may include a timer 148. The timer 148 may also be known as a pulse generator logic circuit. The third method 400 may include receiving a signal through the first device data receiver 108. In a specific example, the signal may be a configuration signal. The first device data receiver 108 may also be known as a power and configuration receiver. As a non-limiting example, the first device data receiver 108 may include a passive envelope detector ED, as shown in FIG. 26. The passive envelope detector ED may advantageously detect data without requiring additional active devices and/or transistors. In a particular embodiment, the received configuration signal may designate a pulse-width and/or a pulse-frequency of the bi-phasic electrical stimulation pulse. Next, a bi-phasic electrical stimulation pulse based on the configuration signal may be generated by the timer and/or the pulse generator logic circuit (not shown). It should be appreciated that more than one bi-phasic electrical stimulation pulse based on the configuration signal may be generated. The bi-phasic electrical stimulation pulse may be coupled to the tissue of the patient. In a specific example, the bi-phasic electrical stimulation pulse may be physically coupled to the tissue of the patient. In another specific example, the bi-phasic electrical stimulation pulse may be coupled to the tissue of the patient through a plurality of first device electrodes 112, thereby enabling bi-phasic electrical stimulation.

III. Example

Figure 21:
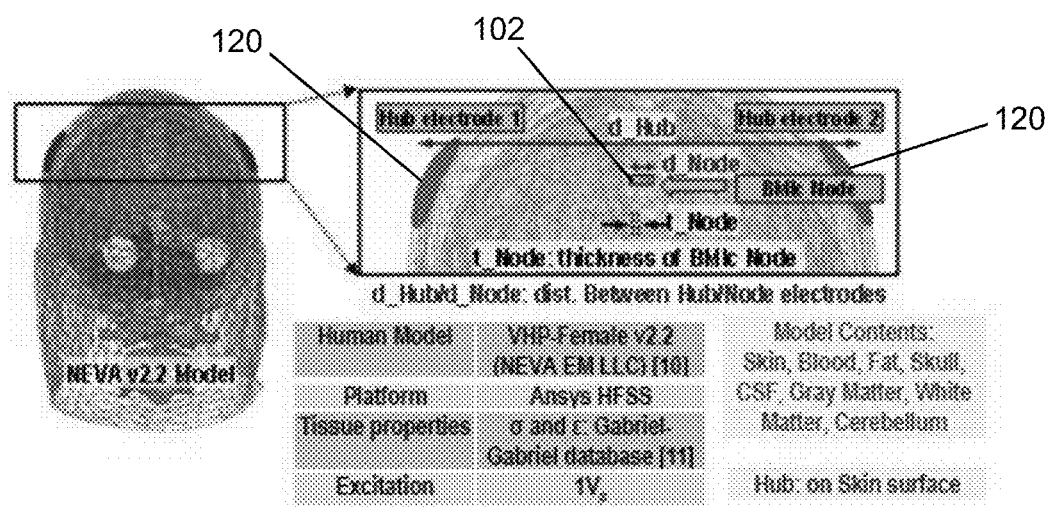
FIG. 21 is a schematic diagram illustrating a simulator setup used to test the channel transfer function (TF) for the wireless communication system utilizing the Bi-Phasic Quasi-Static Brain Communication modality of body channel communication, according to one embodiment of the present disclosure.
Figure 22:
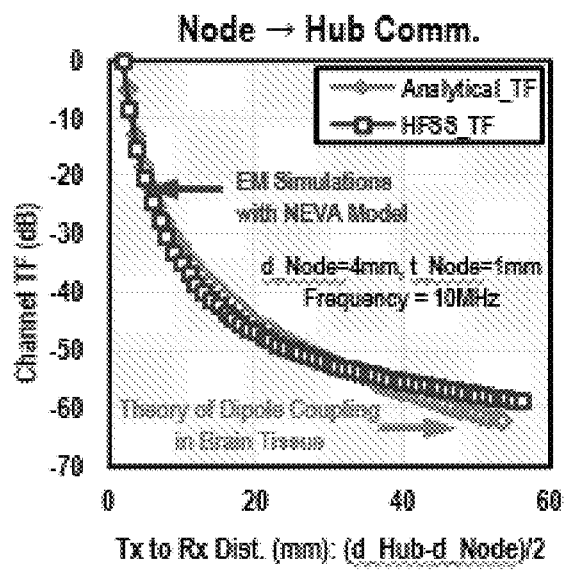
FIG. 22 is a line graph illustrating the channel loss between the first device and the second device, further depicting the consistency of the channel loss to an analytical transfer function obtained from a theory of dipole coupling with a conductive medium, according to one embodiment of the present disclosure.
Figure 24:
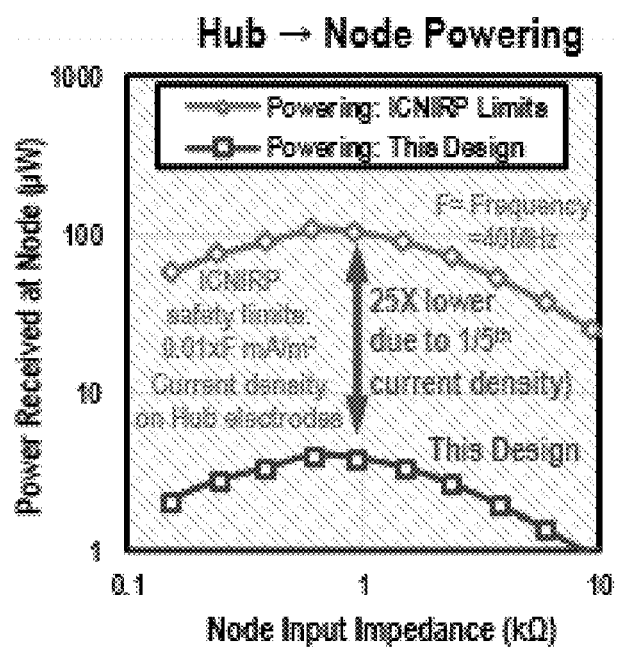
FIG. 24 is a line graph illustrating the first device may be powered with a fraction of the current density threshold indicated by the International Commission on Non-Ionizing Radiation Protection (ICNIRP) guidelines.

Provided as non-limiting examples, FIGS. 21-22 illustrate a channel transfer function TF for BP-QBC that is estimated from finite-element-method (FEM) based simulations in High Frequency Structure Simulator (HFSS) using a NEVA EM v2.2 model. These simulations show a channel loss of around sixty decibels (dB) for a first device 102 to second device 104 channel length CL of around fifty-five millimeters (mm), which is consistent with an analytical transfer function obtained from a theory of dipole coupling within a conductive medium. The analytical transfer function, as well as the channel transfer function TF from HFSS is plotted in FIG. 22, demonstrating a close match. FIG. 23 illustrates the simulation of a differential powering mechanism for power transfer from the second device 104 to the first device 102, which demonstrates one-hundred-fold higher electric field presence in the differential (galvanic) powering scenario as compared to the single-ended (capacitive) powering scenario. As shown in FIG. 24, the powering of the present technology is demonstrated at one-fifth of the current density limits as regulated by the International Commission on Non-Ionizing Radiation Protection (ICNIRP) guidelines.

Figure 29:
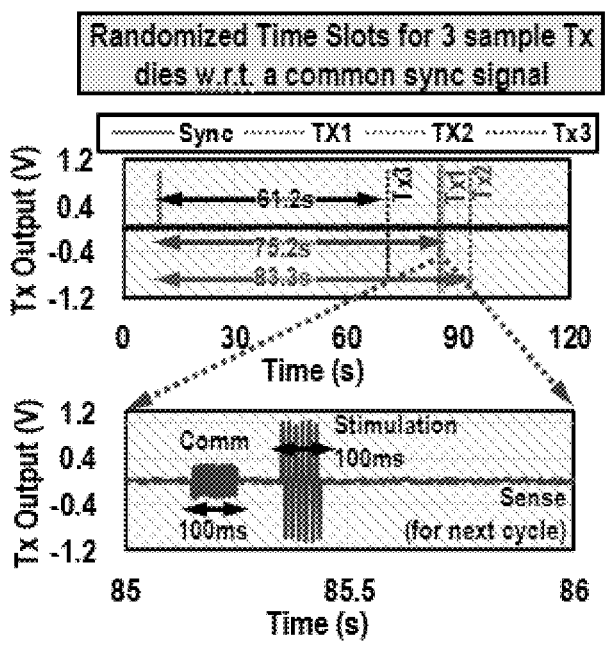
FIG. 29 is a line graph illustrating the randomized time slots for stimulation and communication for the first device, further depicting collision avoidance wherein the first device includes a plurality of implants, according to one embodiment of the present disclosure.
Figure 30:
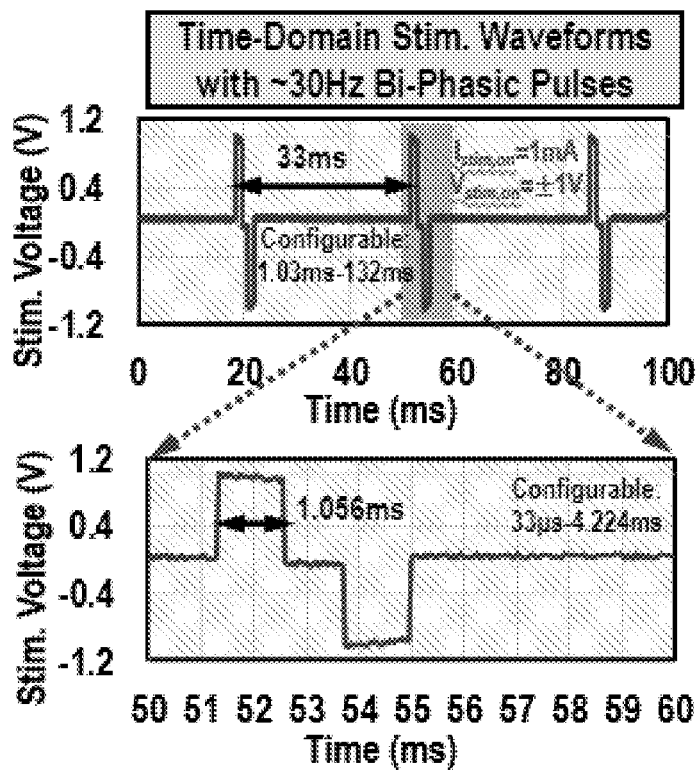
FIG. 30 is a line graph illustrating measured bi-phasic stimulation waveforms for the first device, further depicting the configurable pulse-widths and frequencies, according to one embodiment of the present disclosure.
Figure 38:
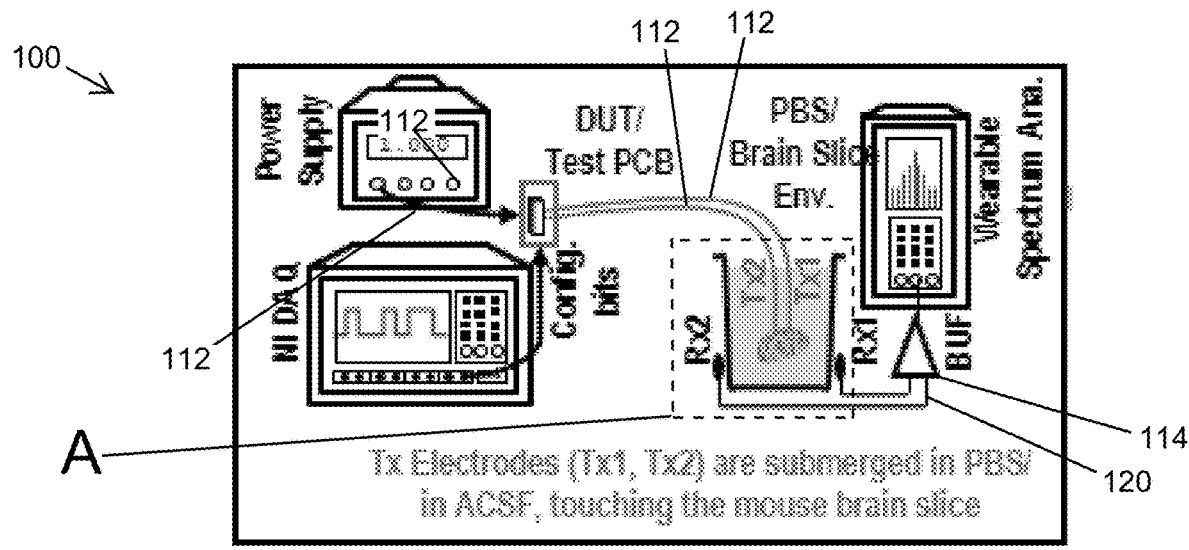
FIG. 38 is a schematic diagram illustrating the setup used to simulate a small-scale use of the Bi-Phasic Quasi-Static Brain Communication modality of body channel communication.
Figure 39:
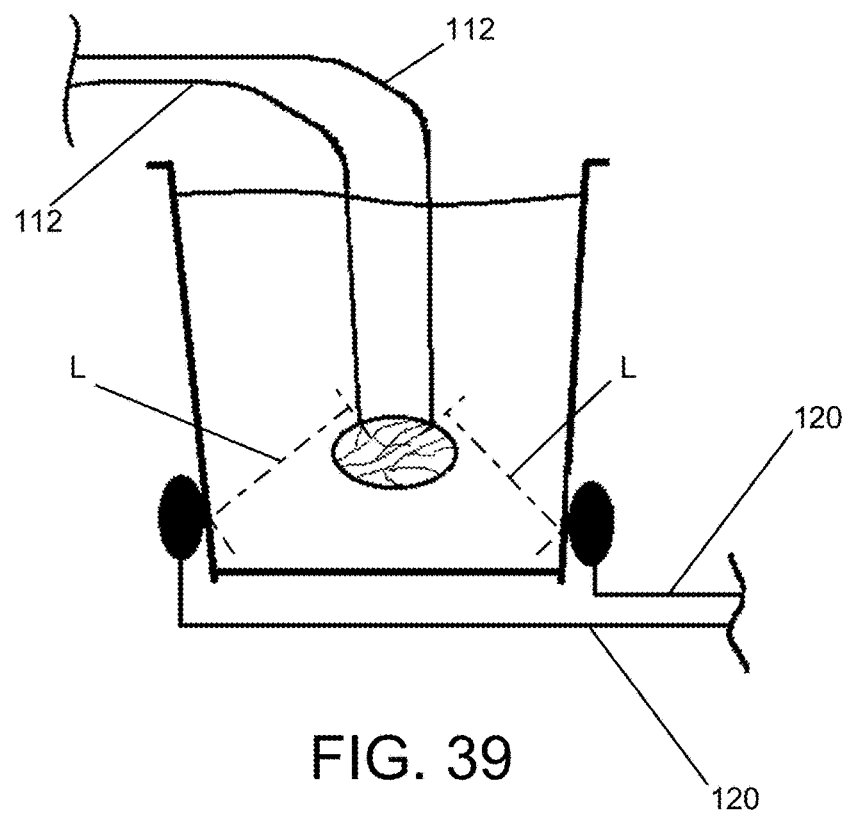
FIG. 39 is an enlarged view of call-out box A from FIG. 38, further depicting a length between the transmitters and the receivers used during the simulation, according to one embodiment of the present disclosure.
Figure 40:
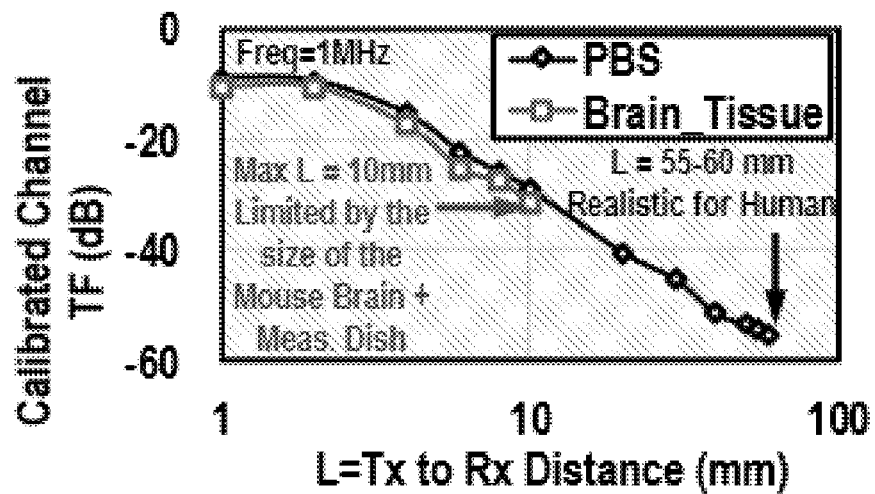
FIG. 40 is a line graph illustrating an achieved channel length in the measurement, as shown in FIGS. 38-39, and further depicting the calculated channel length of the wireless communication system in a human-sized brain, according to one embodiment of the present disclosure.
Figure 41:
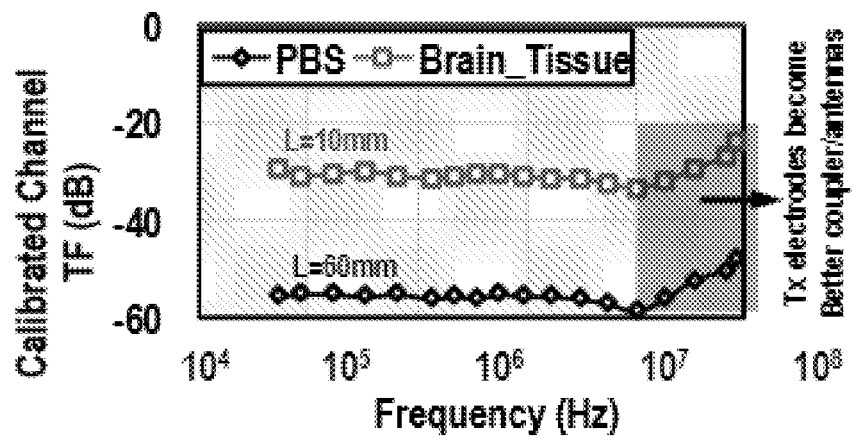
FIG. 41 is a line graph illustrating the channel length achieved in the small-scale simulation, as shown in FIGS. 38-39, and further depicting a calibrated transfer function in phosphate buffered saline.
Figure 42:
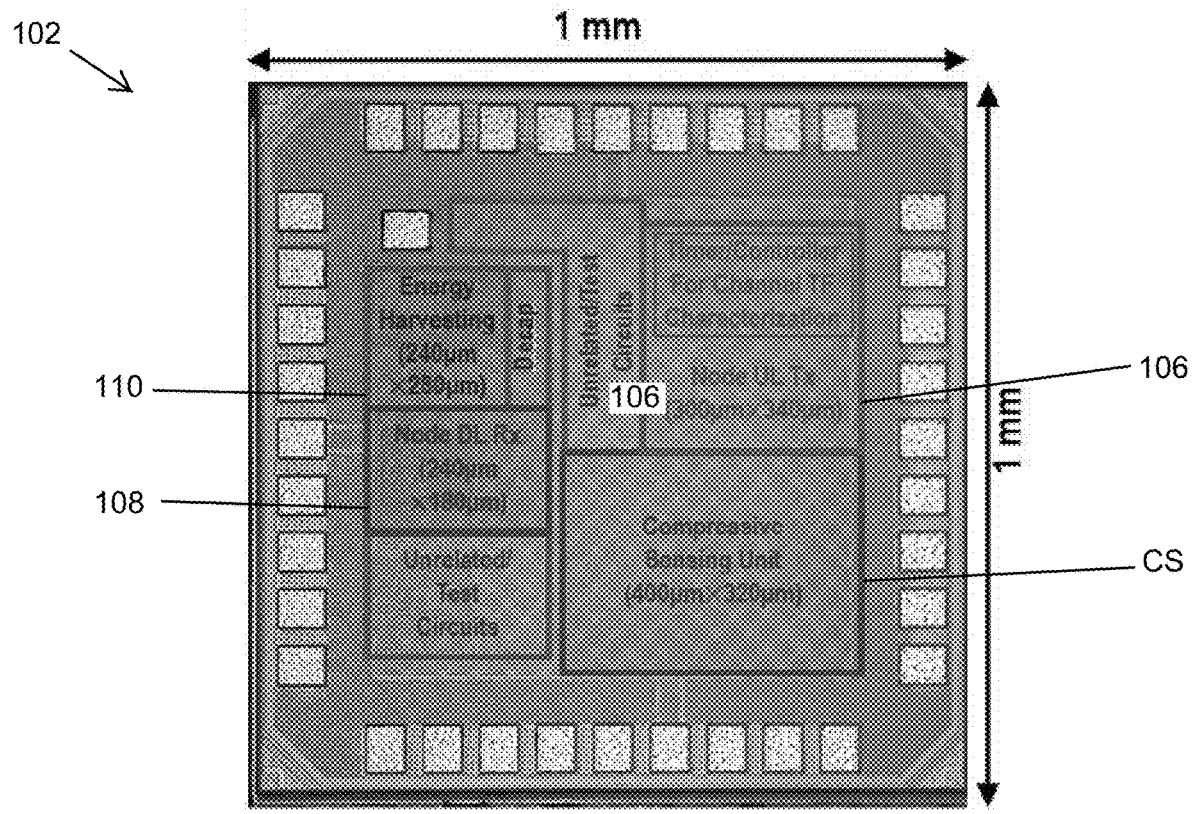
FIG. 42 is a schematic diagram illustrating a chip micrograph of the first device, according to one embodiment of the present disclosure.
Figure 43:
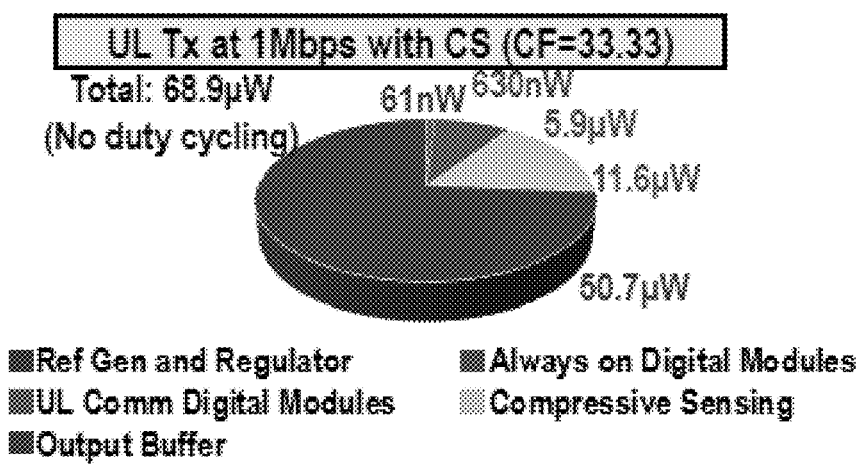
FIG. 43 is a pie chart illustrating the power consumption of the data transmitter on the first device, otherwise known as the uplink transmitter, according to one embodiment of the present disclosure.

Referring to FIGS. 38-41, an in-vitro experimental setup for BP-QBC channel transfer function (TF) measurement is shown. Brain slices from a C57BL/6J mouse strain was used, adhering to the overseeing Animal Care and Use Committee guidelines. As shown in FIGS. 38 and 39, brain slices with thickness ranging from five-hundred micrometers to two millimeters were placed in a measurement dish containing artificial cerebrospinal fluid (CSF) saturated with carbogen (95% O2+5% CO2). Two Ag—AgCl electrodes (signal and reference) were placed on the surface of the brain slice which were connected to the system on a chip (SoC) 124 designed in 65 nm technology and mimics the first device electrodes 112 of the first device data transmitter 106, or otherwise known as the implanted transmitter. The second device data receiver 114, other may be known as the external receiver (Rx), may include a plurality of second device electrodes 120 that were placed at a predetermined distance L from the first device electrodes 112. More specially, the second device electrodes 120 were placed at a predetermined distance L of around ten millimeters from the first device data transmitter 106. The experiments were repeated with phosphate-buffered saline (PBS) in a polyethylene terephthalate (PET) container with similar dimensions as that of the human skull, which includes a diameter around one-hundred ten millimeters. The channel transfer function TF shown in FIG. 41 exhibits a channel loss of around twenty to thirty decibels (dB) for a mouse brain and around sixty decibels (dB) in PBS with human-brain sized dimensions across electro-quasistatic (EQS) frequencies of around ten megahertz (MHz) or less. FIG. 28 depicts the power consumption of the first device data transmitter 106 in the uplink channel UL from 50 kHz to 1 GHz frequencies and compares it with the power consumption of traditional galvanic BCC. It should be appreciated that within 50 kHz to 30 MHz frequencies, the power consumption of BP-QBC first device data transmitter 106 is orders of magnitude lower than a galvanic BCC transmitter. Specifically, with continued reference to FIG. 28, at a frequency of 1 MHz (of the electro-quasistatic carrier signal), BP-QBC offers around forty-one-fold better energy efficiency than galvanic BCC. As non-limiting example, the first device data transmitter 106 may consume around sixty-nine microwatts of power at a data rate of one megabyte per second with compressive sensing, as shown in FIG. 43. Randomized time slots from three different instances of the first device data transmitter 106 are also shown in FIG. 29, with respect to a synchronizing signal. In a more specific, non-limiting example, measured randomized time slots for stimulation and communication from three different implants, Tx1, Tx2 and Tx3, of the first device 102 may demonstrate collision avoidance. With continued reference to the non-limiting example, after a synchronization signal (shown as "Sync" in FIG. 29), the three implants, Tx1, Tx2 and Tx3, send the stimulation and communication signals at three different time slots. The randomized time slots may be governed by the collision avoidance scheme implemented using the ring-oscillator based physical unclonable function circuit 144, as shown in FIG. 20. As shown in FIG. 29, each time slot is shown to have a 100 ms communication slot and a 100 ms stimulation slot, which are separated by 100 ms. Time-domain measured bi-phasic stimulation waveforms are shown in detail in FIG. 30. With continued reference to FIG. 30, the bi-phasic stimulation waveforms may have configurable pulse-widths and frequency. Advantageously, the configurable pulse-widths and frequency may be used for stimulating the brain tissue that enhances the biological signals.

Figure 31:
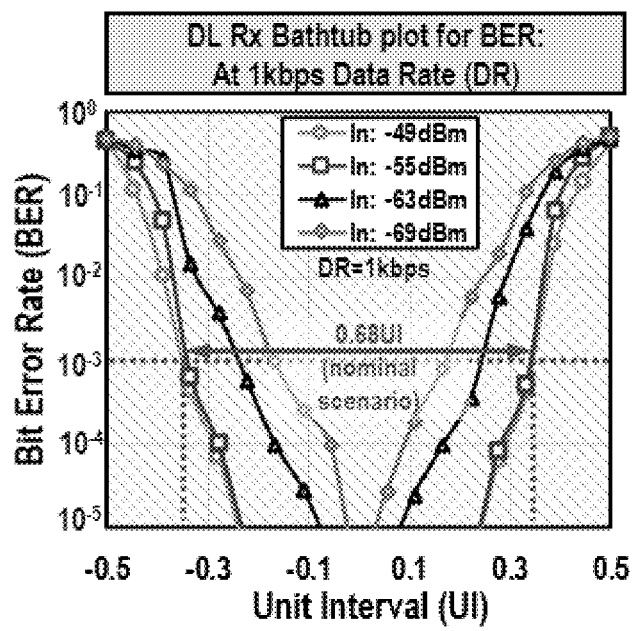
FIG. 31 is a line graph illustrating the performance of the data receiver of the first device, further depicting a relationship between a bit error rate and a timing offset, according to one embodiment of the present disclosure.
Figure 32:
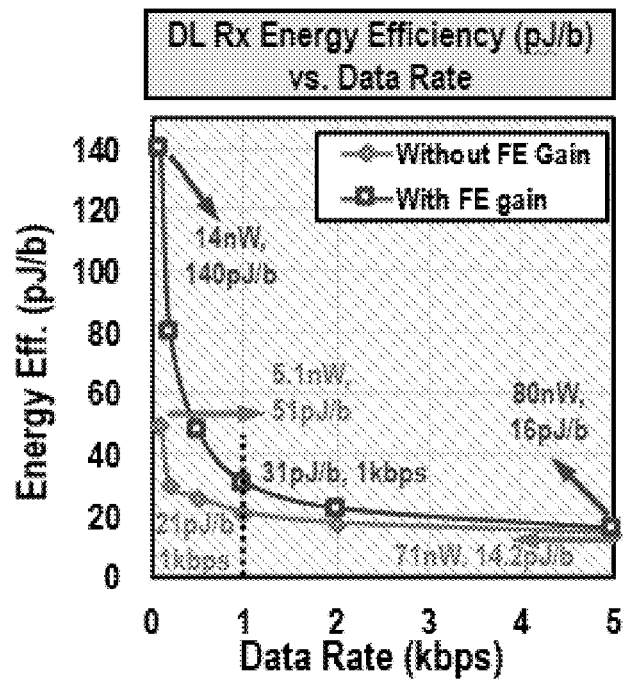
FIG. 32 is a line graph illustrating the energy efficiency of data receiver of the first device as a function of an incoming data rate, according to one embodiment of the present disclosure.

As shown in FIG. 31, the performance of the first device data receiver 108 may be measured by identifying a relationship between a bit error rate and a timing offset. For instance, with continued reference to FIG. 31, the bit error rate (BER) is less than $10^{-3}$ for a large range of timing offset between an incoming data and a clock utilized in the first device data receiver 108, or otherwise known as the downlink receiver. The timing offset is represented in terms of unit intervals which is a ratio of the timing offset and the clock frequency. Turning now to FIG. 32, the first device data receiver 108 may include various ways to enhance energy efficiency depending on an incoming data rate. For instance, if the incoming signal has enough amplitude, a front-end amplifier FE 166 is not necessary at the first device data receiver 108. In a more specific example, as shown in FIG. 32, the first device data receiver 108 may have an energy efficiency of around 21 pJ/bit where the incoming data rate is 1 kbps. Alternatively, for low input signal, a front-end amplifier FE 166 may be used to boost the signal, which would result in an energy efficiency of around 31 pJ/bit.

Figure 33:
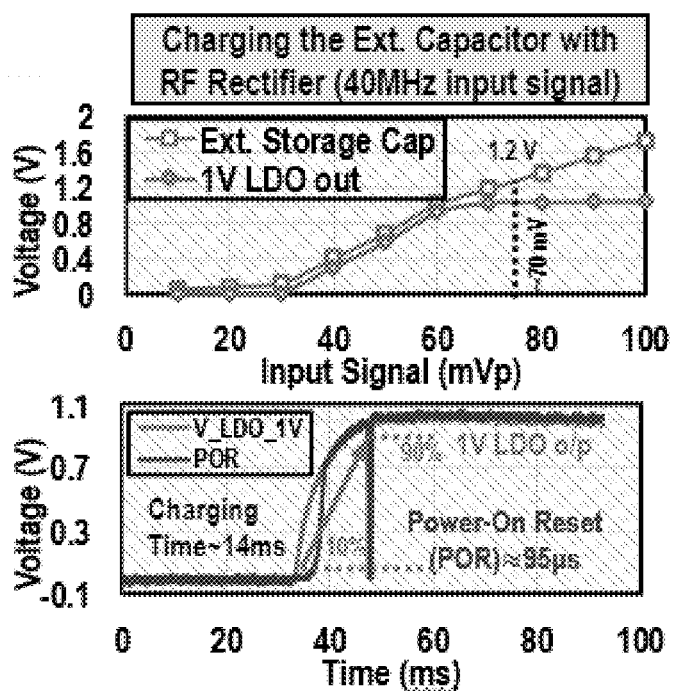
FIG. 33 is a line graph illustrating the changing waveforms of the capacitor of the first device for storing harvested energy, according to one embodiment of the present disclosure.

As shown in FIG. 33, the capacitor 134 of the first device 102 may use changing waveforms in the first device 102 for storing harvested energy. In a specific example, the capacitor 134 may be a 40 μF capacitor that may charge to greater than 1.2V for an input signal amplitude of more than 70 mV. The capacitor 134 may also include a 1V low-dropout regulator's (LDO) output and a power-on reset (POR), as also shown in FIG. 33. The LDO may generate a fixed 1V voltage, that may be used by the communication circuits. The POR may simultaneously generate a reset after powering on the first device 102 to define the states in a digital logic (not shown) present in the first device 102.

Figure 37:
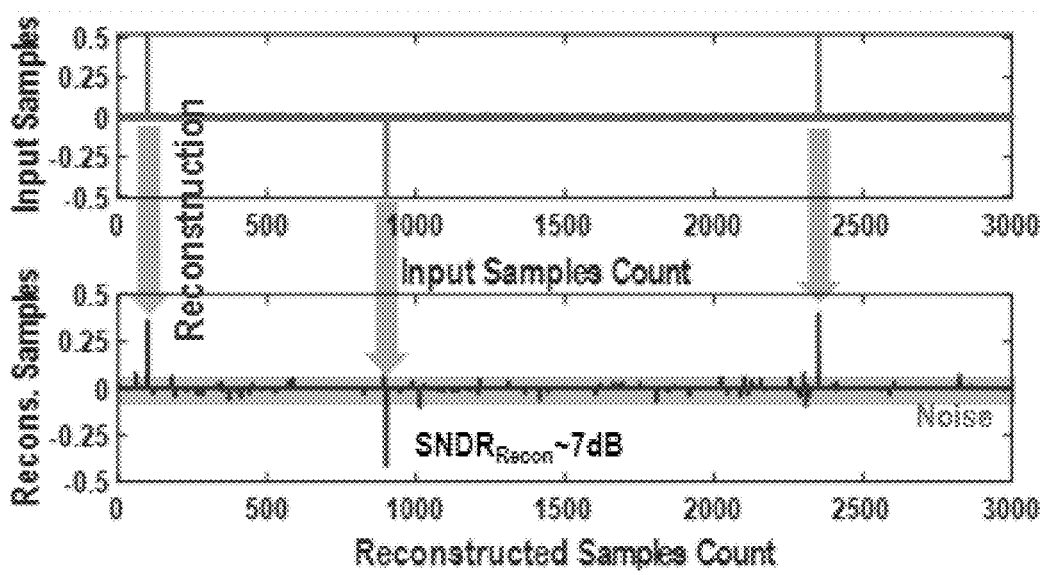
FIG. 37 is a line graph illustrating the performance of the wireless communication system utilizing compressive sensing, according to one embodiment of the present disclosure.

With reference to FIGS. 34-37, the performance of the wireless communication system 100 was enhanced with utilizing compressive sensing. As shown in FIG. 34, in a specific non-limiting example, the compressing sensing capabilities may be provided as a compressive sensing module CS. The compressive sensing module CS may include the stimulator 135 and/or the duty cycled modules 136, 138. In a more specific example, as shown in FIGS. 35-36, where the wireless communication system 100 includes a data rate of around eight megabytes per second, the wireless communication system 100 may have around a sixteen-fold enhancement in power efficiency. With continued reference to FIG. 36, the power conservation of the wireless communication system 100 is still enhanced by more than fifteen-fold over known methods than may even utilize duty-cycling. As shown in FIG. 37, three-thousand input samples from an electro-encephalogram (EEG) waveform were provided as an input to the wireless communication system 100 with compressive sensing, which compressed the digital size of the samples by around five-fold. Advantageously. the EEG waveform of all three-thousand samples may be reconstructed with a signal to noise and distortion ratio (SNDR) of around seven decibels at the second device 104 or at an external server (not shown) such as a computer cloud that may be in communication with the second device 104.

Advantageously, the wireless communication system 100 and method may enhance enable a higher data rate, and enhanced channel length CL, a lower operating power, and an enhanced signal transference efficiency. Without being bound to any particular theory, it is believed the fully electrical quasi-static signaling of the present disclosure militates against energy transduction losses. Desirably, the wireless communication system 100 may also militate against interfering with the physiological signals of the patient or unintentionally stimulating the brain tissue of the patient.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A wireless communication system, comprising:
   a first device including a first device data transmitter, a first device data receiver, and an energy harvester;
   a second device including a second device data receiver, a second device data transmitter, and a power transmitter, the second device is configured to communicate via Bi-Phasic Quasi-Static Brain Communication with the first device;
   a randomizer;
   a timer;
   wherein a wireless communication from the first device to the second device includes an electrical uplink channel and the wireless communication from the second device to the first device includes an electrical downlink channel;
   wherein the first device includes a collision avoidance capability; and
   wherein each of the randomizer and the timer are coupled to the first device and are configured to cooperatively provide a collision avoidance feature.

2. The wireless communication system of claim 1, wherein the electrical downlink channel utilizes a transfer energy ranging from greater than zero microwatts up to about three microwatts.

3. The wireless communication system of claim 1, wherein the uplink channel may be configured to transmit data at 6 kbps to 10 Mbps.

4. The wireless communication system of claim 1, further comprising a stimulator coupled to the first device data transmitter, the stimulator is configured to provide a compressive sensing capability.

5. The wireless communication system of claim 1, further comprising a DC blocking cap coupled to the first device data transmitter.

6. The wireless communication system of claim 1, wherein the first device includes a plurality of first device electrodes, and the first device utilizes dipole coupling to create an electric field between the first device electrodes.

7. The wireless communication system of claim 1, further comprising a charge pump that is coupled to the first device and is configured to militate against leakage of power on the first device.

8. The wireless communication system of claim 1, wherein the communication distance between the first device and the second device may include a channel length up to about fifty-five millimeters.

9. A method of using a wireless communication system through a tissue of a patient, the method comprising steps of:
   providing a first device including a first data transmitter, a first data receiver, an energy harvester, a first device electrode, and a capacitor electrically coupled to the first device electrode, the first device is configured to be substantially implanted within the patient;
   providing a second device including a second device data receiver, a second device data transmitter, and a power transmitter, the second device is configured to be disposed substantially epicutaneously on the patient, the first device is configured to communicate to the second device through an electrical uplink channel and the second device is configured to communicate to the first device through an electrical downlink channel;
   receiving an input signal at the first device;
   processing the input signal into a bi-phasic signal, which includes converting the input signal into a digital data signal at the first device data transmitter;
   modulating the digital data signal into an electro-quasistatic carrier signal and transmitting the modulated electro-quasistatic carrier signal from the first device data transmitter to an output circuit on the first device;
   coupling the modulated electro-quasistatic carrier signal on the tissue of the patient through the first device electrode and transferring the modulated electro-quasistatic carrier signal through the capacitor to generate the bi-phasic signal;
   transmitting the bi-phasic signal through the tissue of the patient; and
   receiving the bi-phasic signal at the second device data receiver.

10. The method of claim 9, wherein the electro-quasistatic carrier signal includes a frequency ranging from fifty kilohertz (kHz) to thirty megahertz (MHz).

11. The method of claim 9, further comprising a step of compressing the digital data signal.

12. The method of claim 9, further comprising a step of transmitting a modulated electro-quasistatic signal at a designated time slot, thereby incorporating a collision avoidance feature.

* * * * *